(12) United States Patent
Sutti

(10) Patent No.: US 11,478,372 B2
(45) Date of Patent: Oct. 25, 2022

(54) STRETCH CORD ASSEMBLIES

(71) Applicant: Kinematic Improvements, LLC, Plano, TX (US)

(72) Inventor: Nathan Joseph Sutti, Plano, TX (US)

(*) Notice: Subject to any disclaimer, the term of this patent is extended or adjusted under 35 U.S.C. 154(b) by 597 days.

(21) Appl. No.: 16/288,853

(22) Filed: Feb. 28, 2019

(65) Prior Publication Data

US 2019/0192327 A1 Jun. 27, 2019

Related U.S. Application Data

(63) Continuation-in-part of application No. 16/100,846, filed on Aug. 10, 2018, now Pat. No. 11,337,845, which is a continuation-in-part of application No. 15/714,817, filed on Sep. 25, 2017, now abandoned, which is a continuation-in-part of application No. 15/133,167, filed on Apr. 19, 2016, now Pat. No. 10,123,897, which is a continuation-in-part of application No. 14/859,107, filed on Sep. 18, 2015, now Pat. No. 10,278,853.

(60) Provisional application No. 62/138,535, filed on Mar. 26, 2015.

(51) Int. Cl.
*A61F 5/00* (2006.01)
*A61F 5/01* (2006.01)
*A61H 1/02* (2006.01)

(52) U.S. Cl.
CPC .......... *A61F 5/0111* (2013.01); *A61H 1/0266* (2013.01); *A61F 2005/0167* (2013.01); *A61H 2201/164* (2013.01)

(58) Field of Classification Search
None
See application file for complete search history.

(56) References Cited

U.S. PATENT DOCUMENTS

| | | | | |
|---|---|---|---|---|
| 5,205,803 A * | 4/1993 | Zemitis | ............... | A63B 21/0552 482/121 |
| 6,868,586 B1 * | 3/2005 | Hall | ................... | A63B 21/0552 24/115 A |
| 7,093,329 B1 * | 8/2006 | Chiu | .................. | A63B 21/0552 24/300 |
| 7,175,574 B2 * | 2/2007 | Carmel | ............ | A63B 21/00185 482/126 |
| 7,458,135 B2 * | 12/2008 | Mikesell | ................ | B25H 3/006 24/300 |
| 7,794,374 B1 * | 9/2010 | Park | ....................... | A63B 23/12 482/122 |
| 9,585,770 B2 * | 3/2017 | Simmons, III | ....... | A43B 3/0015 |
| 10,278,853 B2 * | 5/2019 | Sutti | ........................ | A61H 3/00 |
| 10,371,233 B2 * | 8/2019 | Dershem | ............ | A63B 21/0557 |
| 2012/0267403 A1 * | 10/2012 | Ward, Jr. | .................. | A45F 5/00 224/219 |

(Continued)

*Primary Examiner* — Kim M Lewis
(74) *Attorney, Agent, or Firm* — Miller IP LLC

(57) ABSTRACT

A method, system, apparatus, and/or device for supporting a plantar flexion ridge. The method, system, apparatus, and/or device may include: a sheath; a stretch cord extending along an interior of the sheath from a first end of the sheath to a second end of the sheath; a first buckle attached to a first end of the stretch cord; a first sleeve configured to cover at least a portion of the first end of stretch cord; a second buckle attached to a second end of the stretch cord; and a second sleeve configured to cover at least a portion of the second end of stretch cord.

17 Claims, 15 Drawing Sheets

(56) References Cited

U.S. PATENT DOCUMENTS

2015/0045709 A1\* 2/2015 Wiley .................. A61F 5/0111
602/28

\* cited by examiner

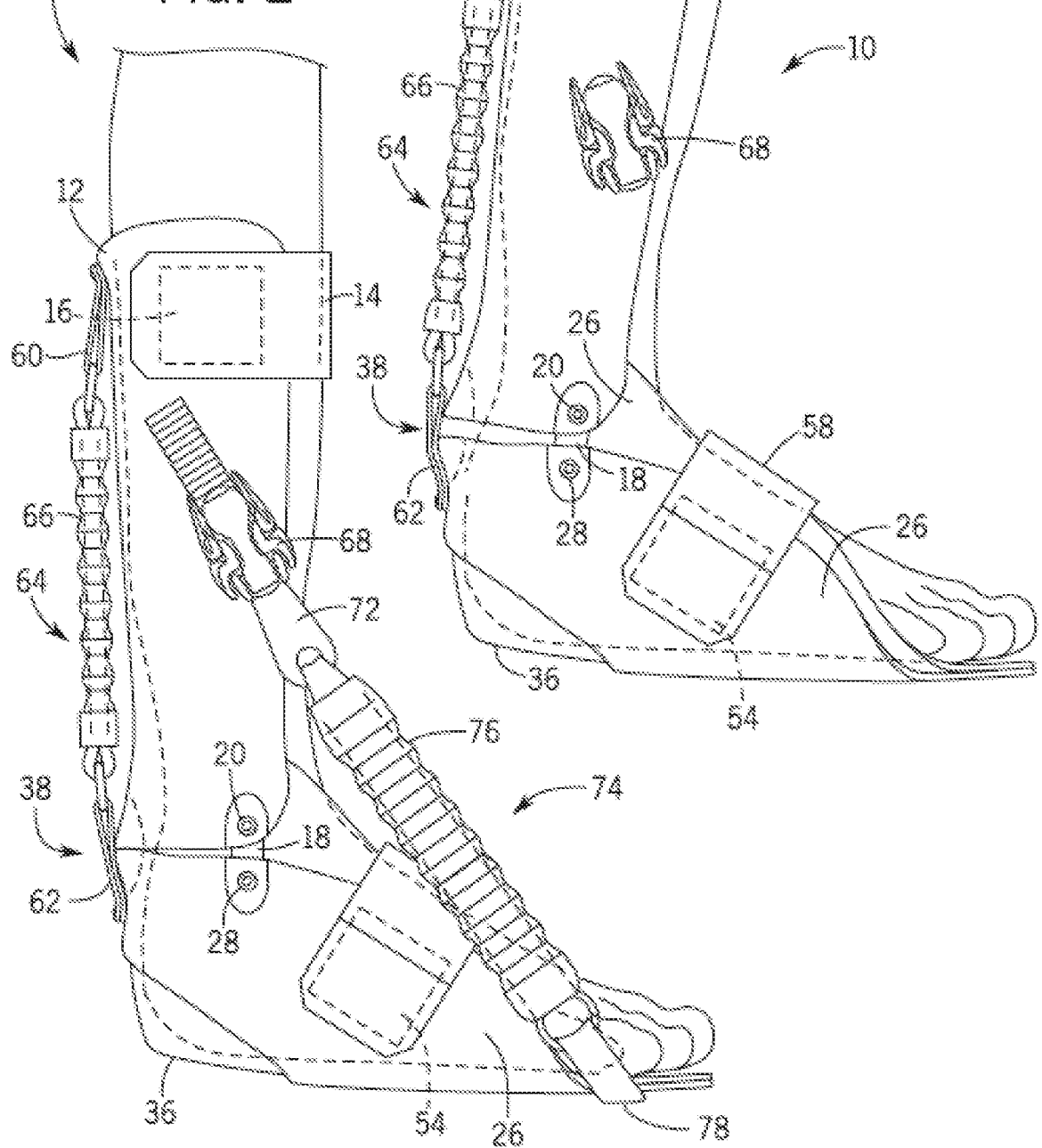

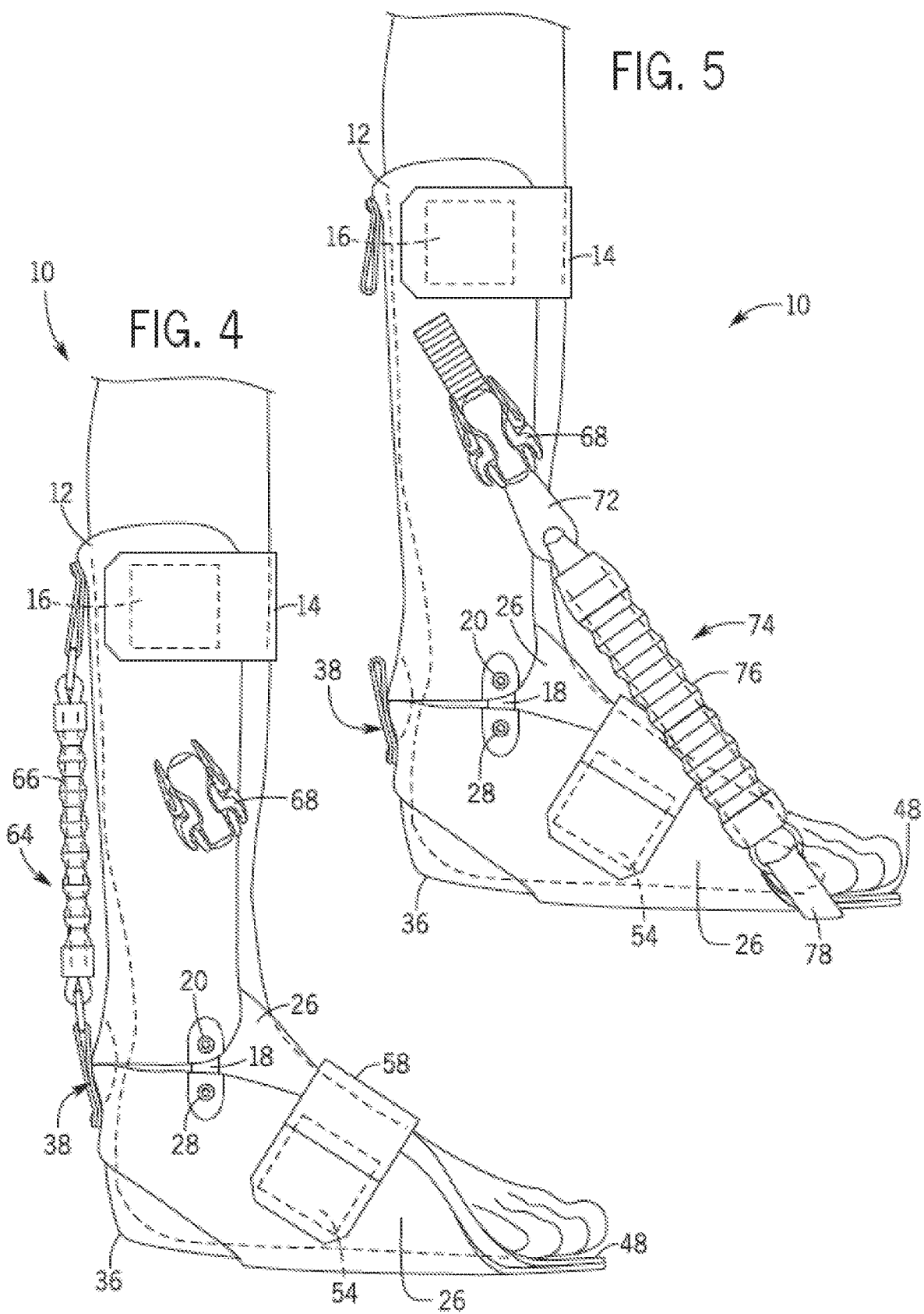

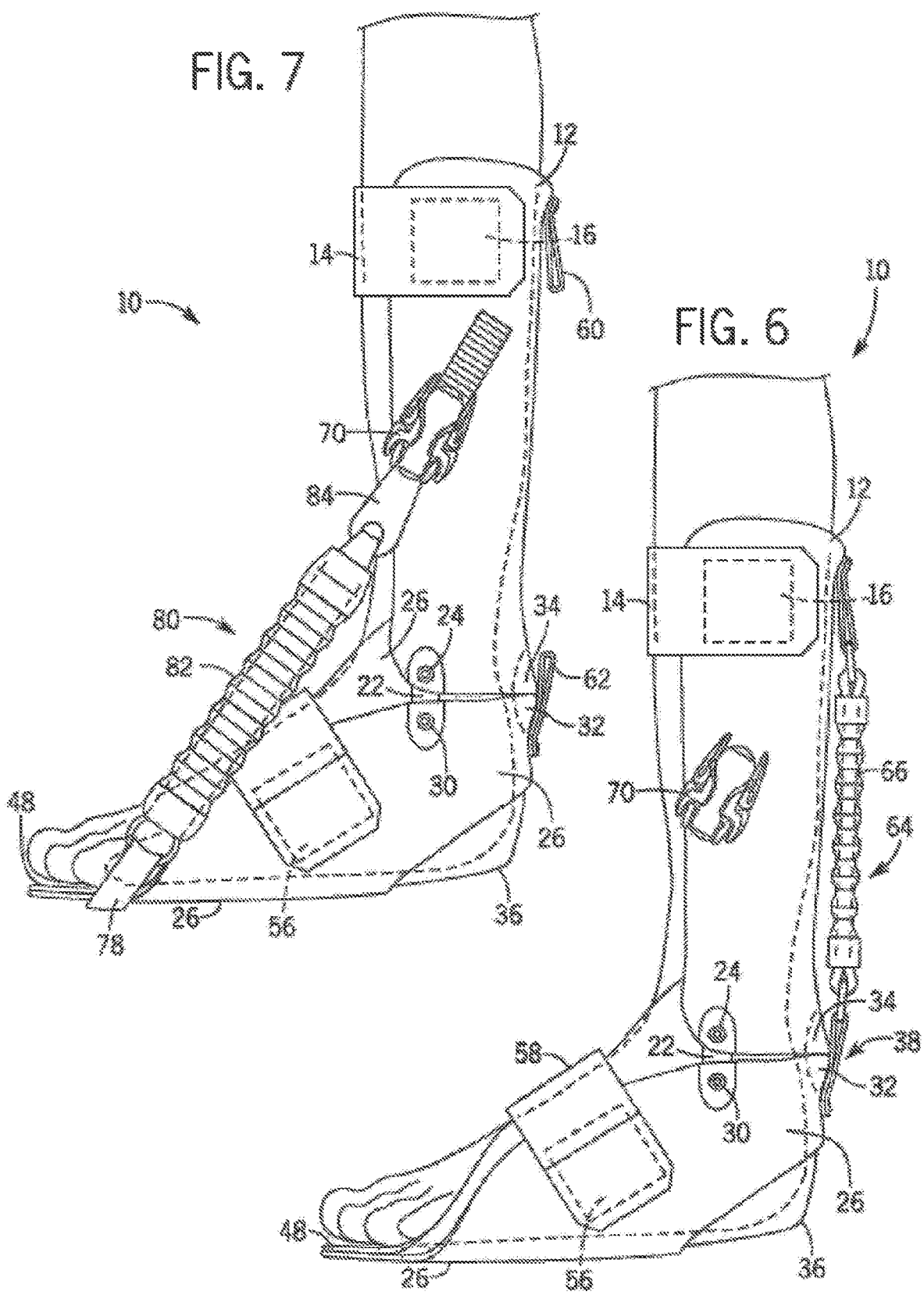

STRETCH CORD ASSEMBLIES

CROSS REFERENCE TO RELATED APPLICATIONS

This application is a continuation-in-part of U.S. non-provisional application Ser. No. 16/100,846, filed Aug. 10, 2018, which is a continuation-in-part of non-provisional patent application U.S. Ser. No. 15/714,817, filed Sep. 25, 2017. This application is a continuation-in-part of U.S. non-provisional application Ser. No. 15/714,817, filed Sep. 25, 2017, which is a continuation-in-part of non-provisional patent application U.S. Ser. No. 15/133,167 filed on Apr. 19, 2016. The non-provisional patent application U.S. Ser. No. 15/133,167 is a continuation-in-part of non-provisional patent application U.S. Ser. No. 14/859,107 filed on Sep. 18, 2015, which, in turn, claims priority to provisional patent application U.S. Ser. No. 62/138,535 filed on Mar. 26, 2015. The entire contents of all applications are herein incorporated by reference.

BACKGROUND

An orthosis is a device used to modify the structural and functional characteristics of the neuromuscular and skeletal system. An orthosis may be used for the correction of disorders of the limbs or spine correct alignment and/or provide support. For example, orthosis may be used to correct alignment and/or provide support to the heel, ankle, and foot of an individual. Examples of simple orthosis devices may include casts, splints, and braces.

BRIEF DESCRIPTION OF THE DRAWINGS

The detailed description of some embodiments of the invention is made below with reference to the accompanying figures, wherein like numerals represent corresponding parts of the figures.

FIG. 2 illustrates a side elevation view perspective view of the dynamic cushion heel-ankle-foot orthosis, according to an embodiment.

FIG. 3 illustrates a side elevation view perspective view of the dynamic cushion heel-ankle-foot orthosis, according to an embodiment.

FIG. 4 illustrates a side elevation view of the dynamic cushion heel-ankle-foot orthosis, according to an embodiment.

FIG. 5 illustrates another side elevation view of the dynamic cushion heel-ankle-foot orthosis, according to an embodiment.

FIG. 6 illustrates another side elevation view of the dynamic cushion heel-ankle-foot orthosis as illustrated in FIGS. 1A-1D, according to an embodiment.

FIG. 7 illustrates another side elevation view of the dynamic cushion heel-ankle-foot orthosis as illustrated in FIGS. 1A-1D, according to an embodiment.

DETAILED DESCRIPTION

Figure 1A:
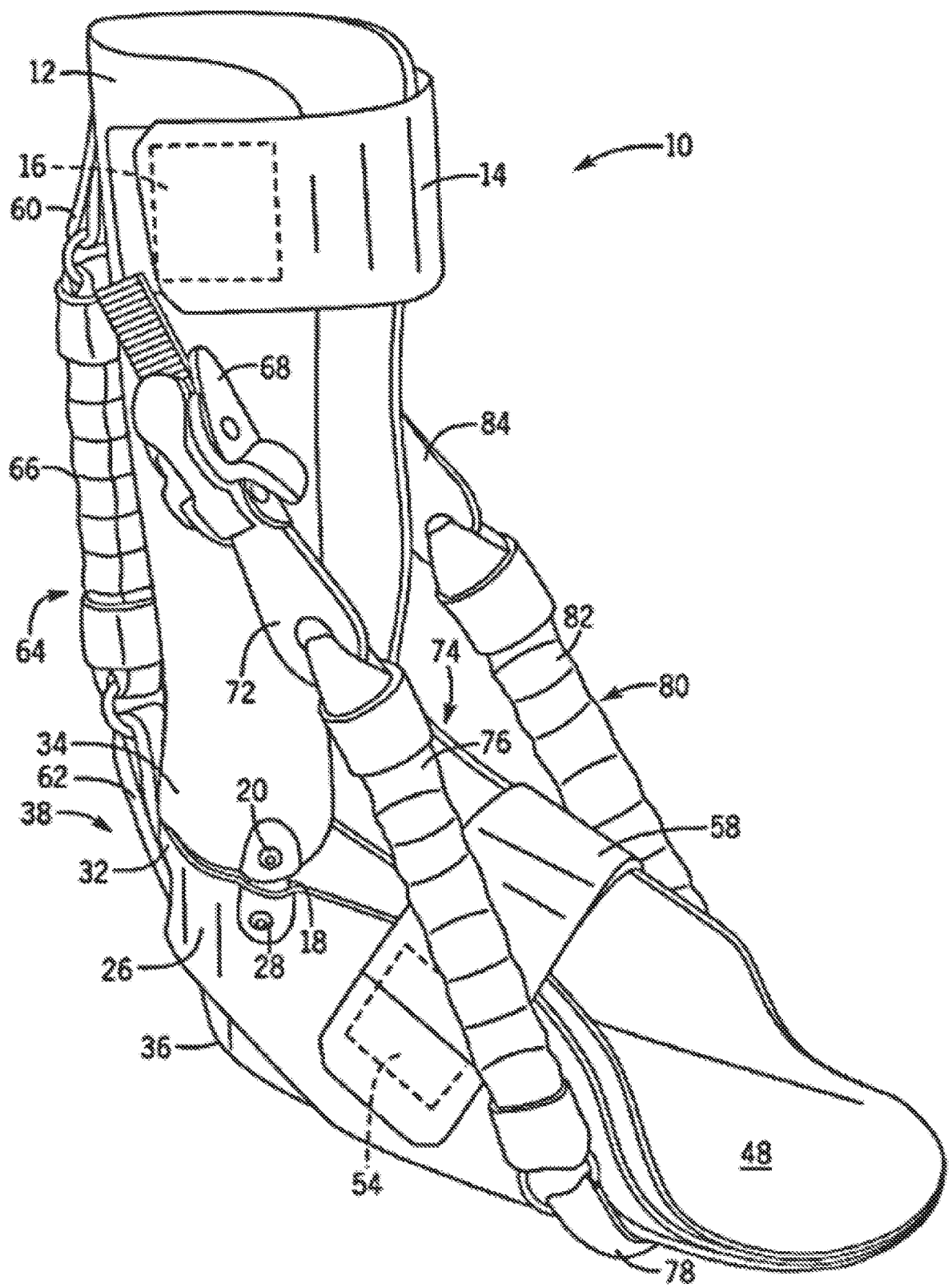
FIG. 1A illustrates a dynamic cushion heel-ankle-foot orthosis comprises leg calf shell attached to leg strap with hook and loop fastener, according to an embodiment.

The disclosed stretch cord assemblies will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, a variety of stretch cord assemblies examples are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

An orthosis may at least immobilize a limb of an individual and protect the limb from further injury. A patient that uses of an orthosis often present with sagittal instabilities which require the use of a plantar flexion stop built into the device. The patient may also have difficulty controlling tibial progression and lack the ability to produce plantarflexion push off in late stance for propulsion and utilization of their third rocker. The patient may also have limited range of motion.

When a plantar flexion stop is used within a conventional orthosis, the plantar flexion stop may create an abrupt knee flexion moment at the initial part of gait which is not part of normal kinematics. Additionally, the plantar flexion stop may be used in cases such as plantar flexion contractures or knee hyperextension. However, conventional orthosis devices may not provide controlled tibial progression, decrease plantarflexion moment at initial contact, and decrease contractures. Furthermore, conventional orthosis devices may not produce an active plantar flexion moment in late stance and stretch contracted muscles, which may be used for both ambulation and therapeutic applications.

Implementations of the disclosure address the above-mentioned deficiencies and other deficiencies by providing a method, a system, a device, and/or an apparatus to provide controlled tibial progression, decrease plantarflexion moment at initial contact, decrease contractures, produce active plantar flexion moments in late stance, and stretch contracted muscles. The method, the system, the device, or the apparatus may utilize an orthotic device with an anterior cord and/or a posterior cord assembly. In one embodiment, a dynamic cushion heel-ankle-foot orthosis system may be configured to provide controlled tibial progression and active plantarflexion in a patient. The dynamic cushion heel-ankle-foot orthosis system may include a leg calf shell that includes a leg calf shell plantar flexion ridge at a lowermost point. A boot shell may be rotatably connected to the leg calf shell and include a boot shell plantar flexion ridge at an uppermost point. The boot shell plantar flexion ridge may contact the leg calf shell plantar flexion ridge at a plantar flexion ridges region and rotate no further.

FIG. 1A illustrates a dynamic cushion heel-ankle-foot orthosis 10 comprises a leg calf shell 12 attached to a leg strap 16 with a hook and a loop fastener, according to an embodiment. The leg calf shell 12 may be attached to the first connecting member 18 with the first connecting member first fastener 20. The leg calf shell 12 is further attached to the second connecting member 22 with the second connecting member first fastener 24. The first connecting member 18 is further attached to the boot shell 26 with the first connecting member second fastener 28. The second connecting member 22 is further attached to the boot shell 26 with the second connecting member second fastener 30.

The upper portion of the boot shell 26 may be a boot shell plantar flexion ridge 32. The lower portion of the leg calf shell 12 may be a leg calf shell plantar flexion ridge 34. When the leg calf shell 12 is rotated toward the heel portion 36, the boot shell plantar flexion ridge 32 may contact the leg calf shell plantar flexion ridge 34 at a plantar flexion ridges region 38 and rotate no further in that direction. In one embodiment, the leg calf shell 12 may rotate counterclockwise toward the heel portion 36 and the boot shell plantar flexion ridge 32. In another embodiment, the leg calf shell 12 may rotate clockwise toward the heel portion 36 and the boot shell plantar flexion ridge 32.

The boot shell 26 may be attached to the first fastener portion 54 and the second fastener portion 56. The first fastener portion 54 and the second fastener portion 56 are attached to the upper portion 58. In one embodiment, the first fastener portion 54 and the second fastener portion 56 may be hook fasteners and a loop fastener may be attached to the upper portion 58. In another embodiment, the upper portion 58 may be adjustable.

A back portion of leg calf shell 12 may be attached to the upper connection loop 60. The boot shell 26 may be attached to the lower connection loop 62. The upper connection loop 60 may be joined to the lower connection loop 62 with the stretch cord assembly 64 which is covered with the stretch cord sheath 66.

The leg calf shell 12 may be attached to the first buckle 68 and the second buckle 70. The first buckle 68 may be adjustably connected to the first connector 72. The first connector 72 may be attached to the first anterior stretch cord assembly 74 covered with the first anterior stretch cord sheath 76. The first anterior stretch cord assembly 74 may be attached to the cord 78. The cord 78 may be attached to the second anterior stretch cord assembly 80 and covered with the first anterior stretch cord sheath 82. The second anterior stretch cord assembly 80 may be attached to the second connector strap 84. The second connector strap 84 may be connected to the second buckle 70.

Figure 1B:
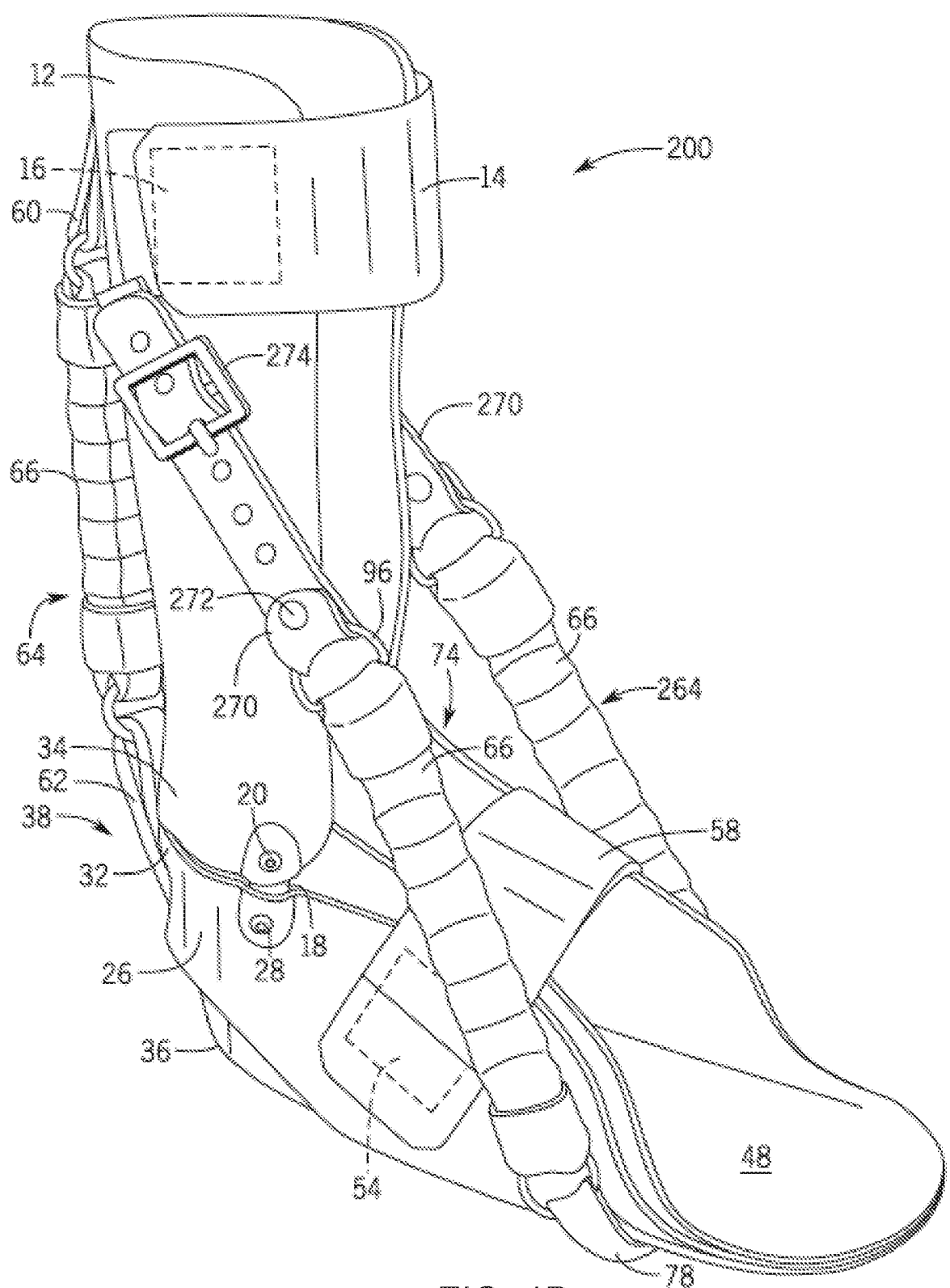
FIG. 1B illustrates a front perspective view of a dynamic cushion heel-ankle-foot orthosis, according to an embodiment.

FIG. 1B illustrates a front perspective view of a dynamic cushion heel-ankle-foot orthosis 200, according to an embodiment. Some of the features in FIG. 1B are the same or similar to some of the features in FIG. 1A as noted by the same reference numbers, unless expressly described otherwise. As discussed above, the back portion of leg calf shell 12 may be attached to the upper connection loop 60 and the boot shell 26 may be attached to the lower connection loop 62. The upper connection loop 60 may be joined to the lower connection loop 62 with the stretch cord assembly 64.

In one embodiment, a front of the leg calf shell 12 may be attached to a front of the boot shell 26 by a fastener. The fastener may include a first portion attached to a side of the leg calf shell 12. The first portion may include a connection strap 270 and a connection buckle 274. The connection buckle 274 may be attached to a side of the leg calf shell 12 and the connection strap 270 may extend toward the boot shell 26. The second portion of the fastener may include the cord 78 connected to a bottom of the boot shell 26 with the stretch cord assembly 64 covered by the stretch cord sheath 66 extending toward an end of the connection strap 270. An end of the stretch cord assembly 64 may include a ring 96.

A portion of the connection strap 270 may extend through the first ring 96 and a rivet 272 may then fasten the connection strap 270 to itself and form a loop that secures the connection strap 270 to the stretch cord assembly 64. In one embodiment, the dynamic cushion heel-ankle-foot orthosis 200 may include a single fastener to connect the front of the leg calf shell 12 to the front of the boot shell 26. In another embodiment, the dynamic cushion heel-ankle-foot orthosis 200 may include a first fastener to connect the front of the leg calf shell 12 to the front of the boot shell 26 at a first side of the dynamic cushion heel-ankle-foot orthosis 200 and a second fastener to connect the front of the leg calf shell 12 to the front of the boot shell 26 at a second side of the dynamic cushion heel-ankle-foot orthosis 200.

Figure 1C:
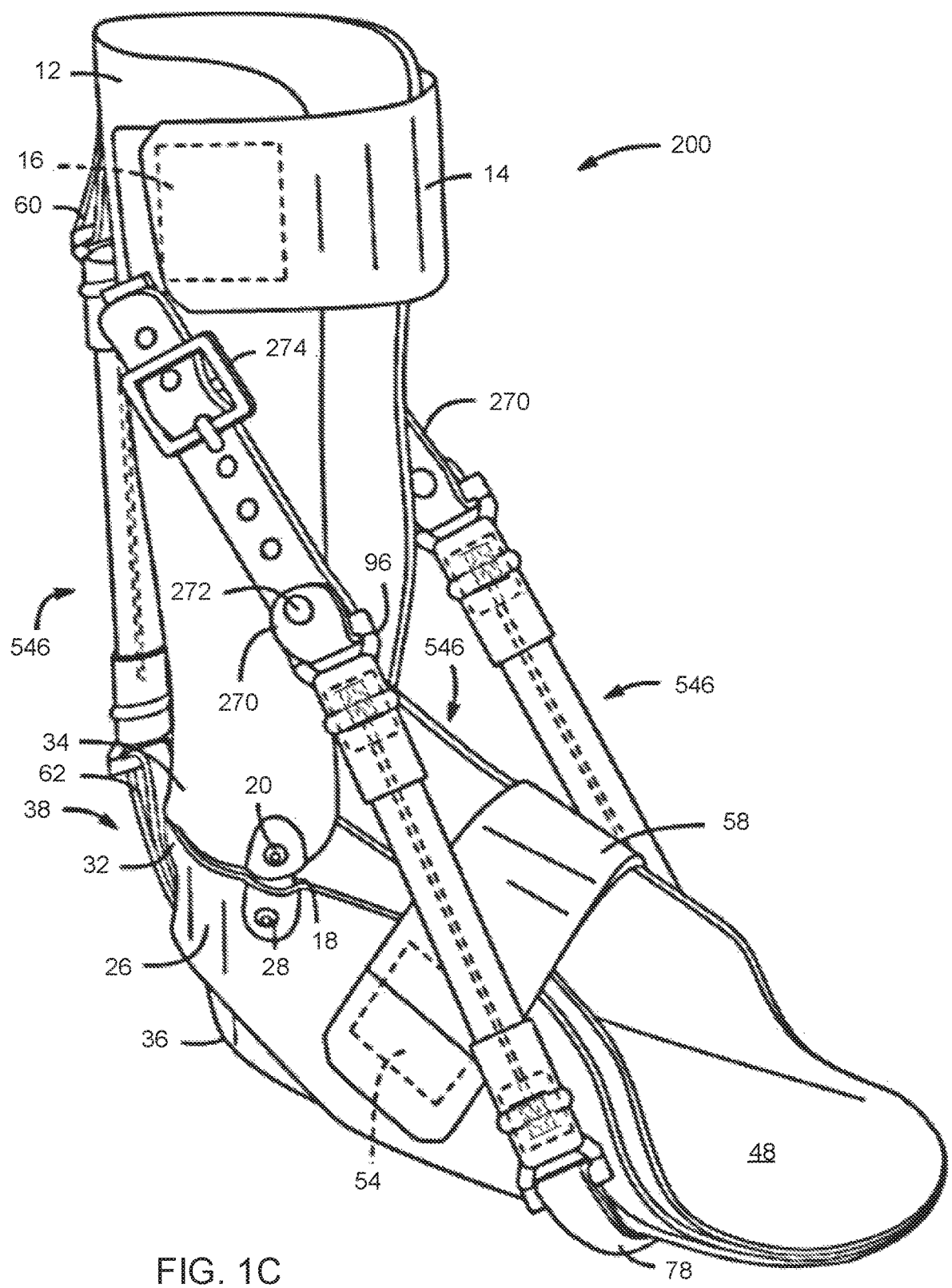
FIG. 1C illustrates a front perspective view of the dynamic cushion heel-ankle-foot orthosis in FIG. 1B with a strap, according to an embodiment.

FIG. 1C illustrates a front perspective view of the dynamic cushion heel-ankle-foot orthosis 200 with a stretch cord assembly 546, according to an embodiment. Some of the features in FIG. 1C are the same or similar to some of the features in FIGS. 1A and 1B as noted by the same reference numbers, unless expressly described otherwise. In one embodiment, the back of the leg calf shell 12 may be connected to the back of the boot shell 26 by a stretch cord assembly 546. The stretch cord assembly 546 may include a variety of configurations, as illustrated in FIGS. 19A-E.

In one embodiment, a front of the leg calf shell 12 may be attached to a front of the boot shell 26 by a fastener. The fastener may include a first portion attached to a side of the leg calf shell 12. The first portion may include the connection strap 270 and the connection buckle 274, as discussed in FIG. 1B. The second portion of the fastener may include the cord 78 connected to a bottom of the boot shell 26 with another stretch cord assembly 546 extending toward an end of the connection strap 270. In one embodiment, the cord 78 may be a flat nylon cord connecting the stretch cord assembly 546 to the bottom of the boot shell 26. In combination, the connection strap 270, the stretch cord assembly 546, and the cord 78 may connect the side of the leg calf shell 12 to the bottom of the boot shell 26.

An end of the stretch cord assembly 546 may include the first ring 96. A portion of the connection strap 270 may extend through the first ring 96 and a rivet 272 may then fasten the connection strap 270 to itself and form a loop that secures the connection strap 270 to the stretch cord assembly 546. In one embodiment, the dynamic cushion heel-ankle-foot orthosis 200 may include a single fastener to connect the front of the leg calf shell 12 to the front of the boot shell 48. In another embodiment, the dynamic cushion heel-ankle-foot orthosis 200 may include a first fastener to connect the front of the leg calf shell 12 to the front of the boot shell 26 at a first side of the dynamic cushion heel-ankle-foot orthosis 200 and a second fastener to connect the front of the leg calf shell 12 to the front of the boot shell 26 boot shell 48 at a second side of the dynamic cushion heel-ankle-foot orthosis 200.

Figure 1D:
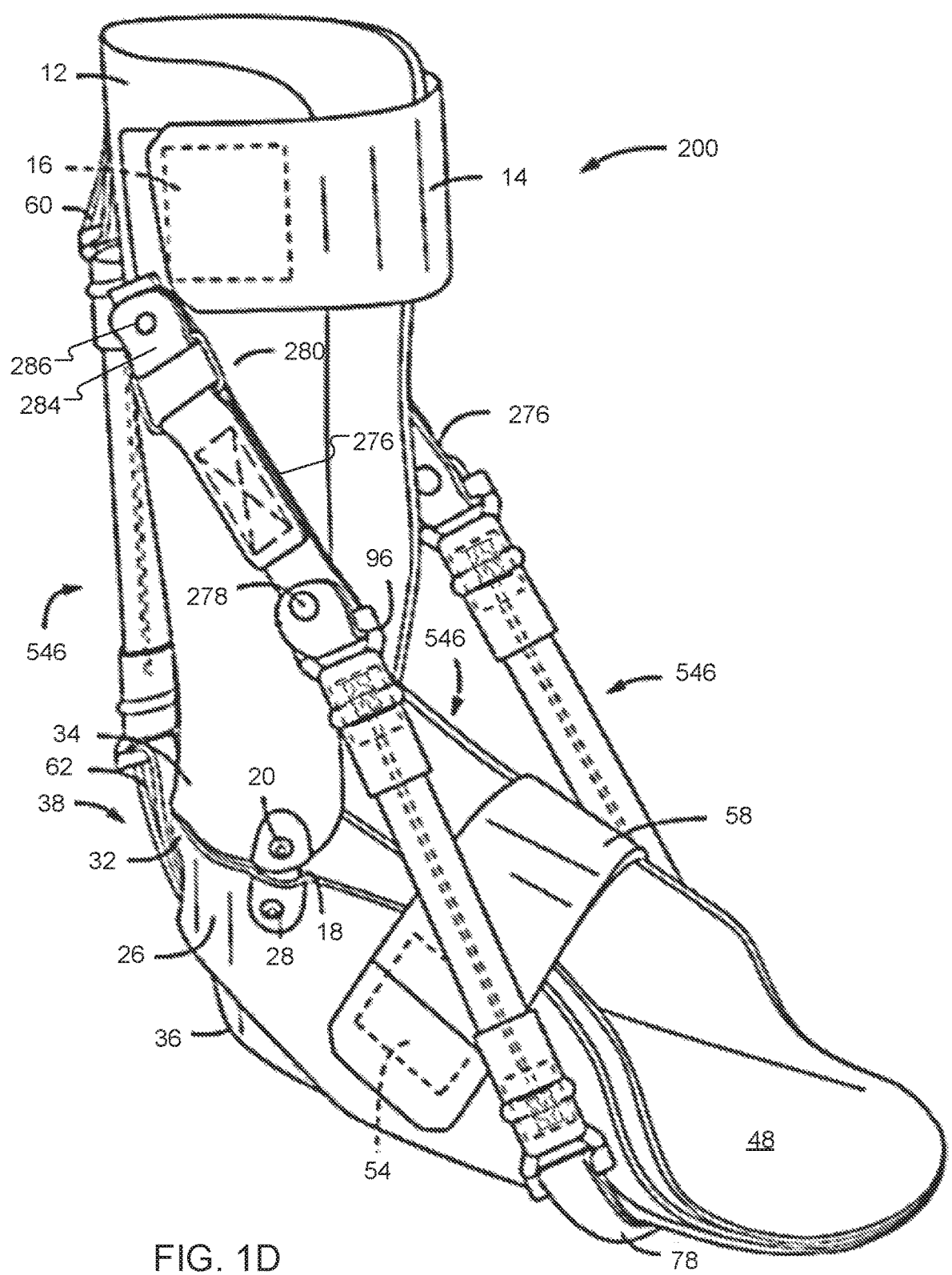
FIG. 1D illustrates a front perspective view of another dynamic cushion heel-ankle-foot orthosis in FIG. 1C with a connector, according to an embodiment.

FIG. 1D illustrates a front perspective view of the dynamic cushion heel-ankle-foot orthosis 200 in FIG. 1C with a first connector 276, according to an embodiment. Some of the features in FIG. 1D are the same or similar to some of the features in FIG. 1A-1C as noted by the same reference numbers, unless expressly described otherwise.

In one embodiment, a front of the leg calf shell 12 may be attached to a front of the boot shell 26 by a fastener. The fastener may include a first portion attached to a side of the leg calf shell 12. The first portion may include the first connector 276, a connection ring 280, and an attachment loop 284. The attachment loop 284 may be a piece material that overlaps itself to form a loop that may be fastened to the leg calf shell 12 by a first fastener 286, such as a rivet, a pin, a nail, a screw, and so forth. The connection ring 280 may be located within the loop of the attachment loop 284 and secured within the loop by the first fastener 286. The attachment loop 284 may be connected to a first end of the connector 276. In one embodiment, the connector 276 may include hooks and loops (such as Velcro®) that may fasten around the attachment loop 284. In one example, the first end of the connector 276 may be attached to the connection ring 280 by a portion of the connector 276 that overlaps itself to form a loop that may be fastened around the attachment loop 284 by a second fastener 278, such as a rivet, a pin, a nail, a screw, and so forth. A second end of the second fastener 278 may be attached to the stretch cord assembly 546, as illustrated and discussed in FIG. 1C. The stretch cord assembly 546 may include a variety of configurations as illustrated in FIGS. 19A-E.

FIG. 2 illustrates a side elevation view perspective view of the dynamic cushion heel-ankle-foot orthosis 10, according to an embodiment. Some of the features in FIG. 2 are the same or similar to some of the features in FIG. 1A-1D as noted by the same reference numbers, unless expressly described otherwise. In one embodiment, when the leg calf shell 12 may rotate counterclockwise toward the heel portion 36, the boot shell plantar flexion ridge 32 may contact the leg calf shell plantar flexion ridge 34 at a plantar flexion ridges region 38 and rotates no further in that direction. In another embodiment, the leg of the user may be in a perpendicular position in the dynamic cushion heel-ankle-foot orthosis 10, where the leg of the user is approximately at a 90-degree angle relative to the foot of the user (as illustrated in FIG. 2).

FIG. 3 illustrates a side elevation view perspective view of the dynamic cushion heel-ankle-foot orthosis 10, according to an embodiment. Some of the features in FIG. 3 are the same or similar to some of the features in FIG. 1A-2 as noted by the same reference numbers, unless expressly described otherwise. In one embodiment, the dynamic cushion heel-ankle-foot orthosis 10 may not include the stretch cord assembly 74 and the connector 72 in FIG. 1A. In another embodiment, the leg of the user may rotate into a forward position in the dynamic cushion heel-ankle-foot orthosis 10, where the leg of the user is at less than a 90-degree angle relative to the foot of the user.

FIG. 4 illustrates a side elevation view of the dynamic cushion heel-ankle-foot orthosis 10, according to an embodiment. Some of the features in FIG. 4 are the same or similar to some of the features in FIG. 1A-3 as noted by the same reference numbers, unless expressly described otherwise. In one embodiment, the dynamic cushion heel-ankle-foot orthosis 10 may not include the stretch cord assembly 74 and the first connector 72 in FIG. 1A. In another embodiment, the leg of the user may be in a perpendicular position in the dynamic cushion heel-ankle-foot orthosis 10, where the leg of the user is approximately at a 90-degree angle relative to the foot of the user.

FIG. 5 illustrates another side elevation view of the dynamic cushion heel-ankle-foot orthosis 10, according to an embodiment. Some of the features in FIG. 5 are the same or similar to some of the features in FIG. 1A-4 as noted by the same reference numbers, unless expressly described otherwise. In one embodiment, the dynamic cushion heel-ankle-foot orthosis 10 may not include the stretch cord assembly 64 in FIG. 1A. In another embodiment, the leg of the user may be in a perpendicular position in the dynamic cushion heel-ankle-foot orthosis 10, where the leg of the user is approximately at a 90-degree angle relative to the foot of the user. The different configuration of the dynamic cushion heel-ankle-foot orthosis 10 and the position of the leg and foot of the user may vary for different applications. In one example, a user may use the dynamic cushion heel-ankle-foot orthosis 10 as illustrated in FIG. 3 or 4 during the day to allow the leg of the user to move between the perpendicular position and the forward position as the user uses his/her leg. In another example, a user may use the dynamic cushion heel-ankle-foot orthosis 10 during the night to allow the leg of the user to remain in the perpendicular position as the user sleeps.

FIG. 6 illustrates another side elevation view of the dynamic cushion heel-ankle-foot orthosis as illustrated in FIGS. 1A-ID, according to an embodiment. Some of the features in FIG. 6 are the same or similar to some of the features in FIG. 1A-5 as noted by the same reference numbers, unless expressly described otherwise. In one embodiment, when the leg calf shell 12 is rotated clockwise towards the heel portion 36, the boot shell plantar flexion ridge 32 may contact leg calf shell plantar flexion ridge 34 at a plantar flexion ridges region 38 and rotates no further in that direction.

FIG. 7 illustrates another side elevation view of the dynamic cushion heel-ankle-foot orthosis as illustrated in FIGS. 1A-ID, according to an embodiment. Some of the features in FIG. 7 are the same or similar to some of the features in FIG. 1A-6 as noted by the same reference numbers, unless expressly described otherwise. In one embodiment, the dynamic cushion heel-ankle-foot orthosis 10 may not include the stretch cord assembly 74 and the connector 72, as it rotates clockwise.

Figure 8:
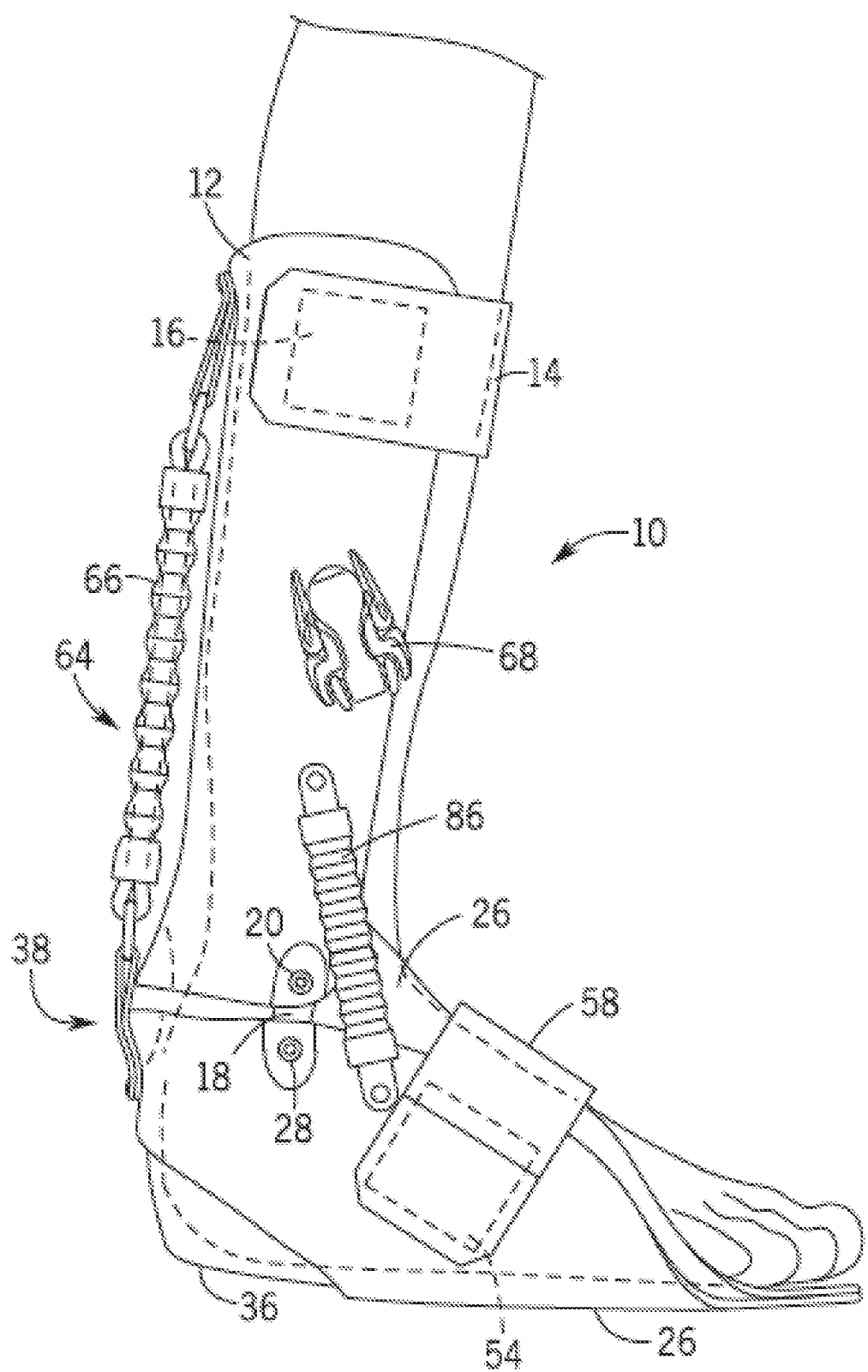
FIG. 8 illustrates another side elevation view of the dynamic cushion heel-ankle-foot orthosis as illustrated in FIGS. 1A-1D, according to an embodiment.

FIG. 8 illustrates another side elevation view of the dynamic cushion heel-ankle-foot orthosis as illustrated in FIGS. 1A-ID, according to an embodiment. Some of the features in FIG. 8 are the same or similar to some of the features in FIG. 1A-7 as noted by the same reference numbers, unless expressly described otherwise. In one embodiment, a direct attachment cord 86 may be used to connect the leg calf shell 12 as it is rotated clockwise towards the heel portion 36 without regard for buckles or cords.

FIGS. 9-16 illustrate a process for making a stretch cord assembly 64. The process for making the stretch cord assembly 64 may include the steps as discussed below for FIGS. 9-16. The order of the steps is not intended to be limiting and may vary.

Figure 9:
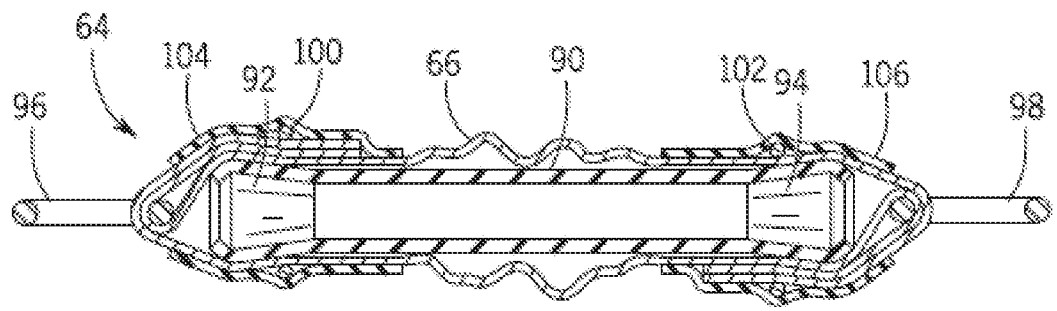
FIG. 9 illustrates a stretch cord assembly, according to an embodiment.

FIG. 9 illustrates a stretch cord assembly 64, according to an embodiment. Some of the features in FIG. 9 are the same or similar to some of the features in FIG. 1A-8 as noted by the same reference numbers, unless expressly described otherwise. The stretch cord assembly 64 may include a hollow cord 90, a first retainer end 92, and second retainer end 94. The stretch cord assembly 64 may include a stretch cord sheath 66, a first ring 96, and second ring 98. The stretch cord assembly 64 may include a first clip 100 and second clip 102. The stretch cord assembly 64 may include a first rubber sleeve 104 and a second rubber sleeve 106. The stretch cord assembly 64 may include a first connector 72.

Figure 10:
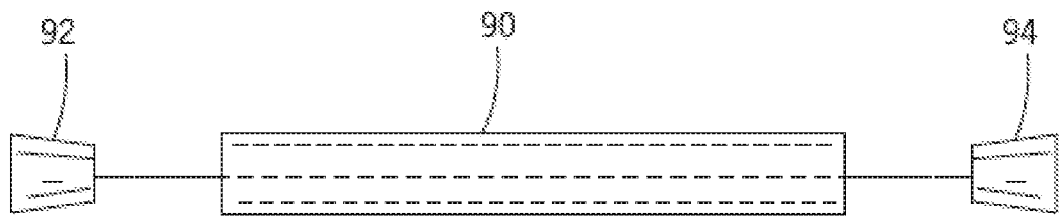
FIG. 10 illustrates a process step in constructing the stretch cord assembly in FIG. 9, according to an embodiment.

FIG. 10 illustrates a process step in constructing the stretch cord assembly 64 in FIG. 9, according to an embodiment. Some of the features in FIG. 10 are the same or similar to some of the features in FIG. 9 as noted by the same reference numbers, unless expressly described otherwise. As discussed above, the stretch cord assembly 64 may include a hollow cord 90. The process may include inserting a first retainer end 92 and a second retainer end 94 into hollow cord 90.

Figure 11:
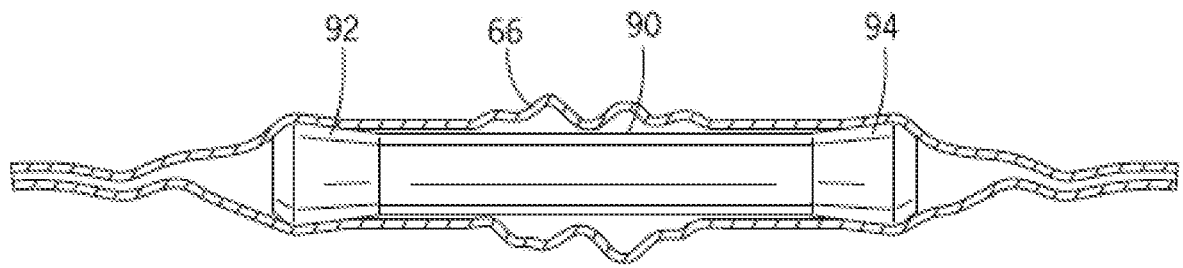
FIG. 11 illustrates another process step in constructing the stretch cord assembly in FIG. 9, according to an embodiment.

FIG. 11 illustrates another process step in constructing the stretch cord assembly 64 in FIG. 9, according to an embodiment. Some of the features in FIG. 11 are the same or similar to some of the features in FIGS. 9-10 as noted by the same reference numbers, unless expressly described otherwise. The process may include sliding the stretch cord sheath 66 over the hollow cord 90.

Figure 12:
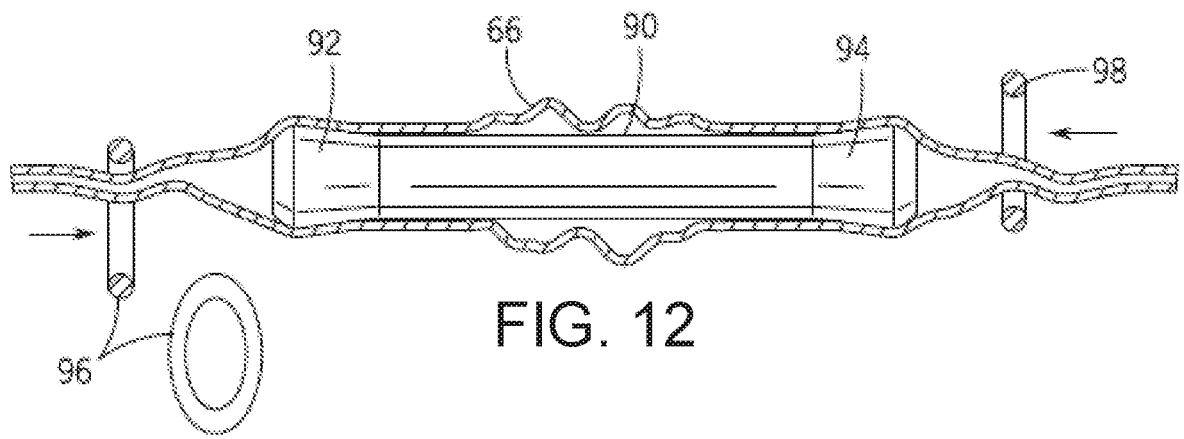
FIG. 12 illustrates another process step in constructing the stretch cord assembly in FIG. 9, according to an embodiment.

FIG. 12 illustrates another process step in constructing the stretch cord assembly 64 in FIG. 9, according to an embodiment. Some of the features in FIG. 12 are the same or similar to some of the features in FIGS. 9-11 as noted by the same reference numbers, unless expressly described otherwise. The process may include wrapping the stretch cord sheath 66 around the first ring 96 and second ring 98.

Figure 13:
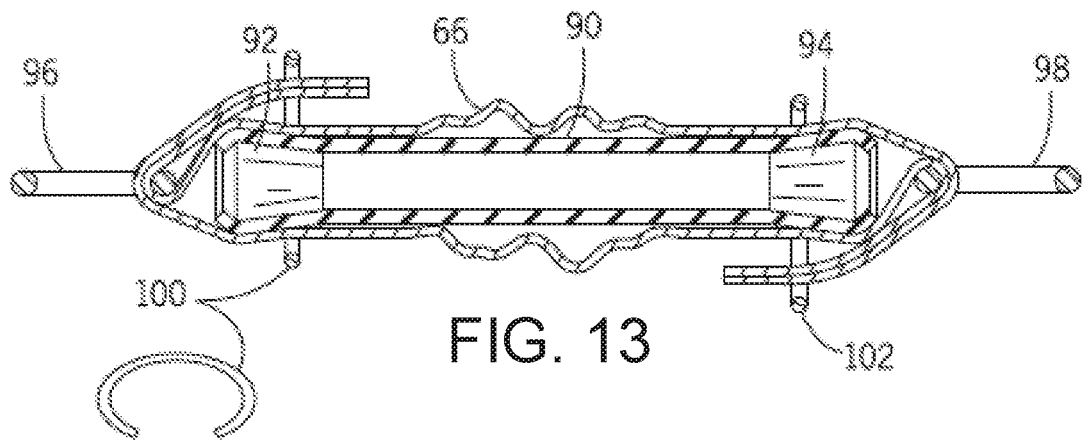
FIG. 13 illustrates another process step in constructing the stretch cord assembly in FIG. 9, according to an embodiment.

FIG. 13 illustrates another process step in constructing the stretch cord assembly 64 in FIG. 9, according to an embodiment. Some of the features in FIG. 13 are the same or similar to some of the features in FIGS. 9-12 as noted by the same reference numbers, unless expressly described otherwise. The process may include holding the stretch cord sheath 66 with the first clip 100 and the second clip 102.

Figure 14:
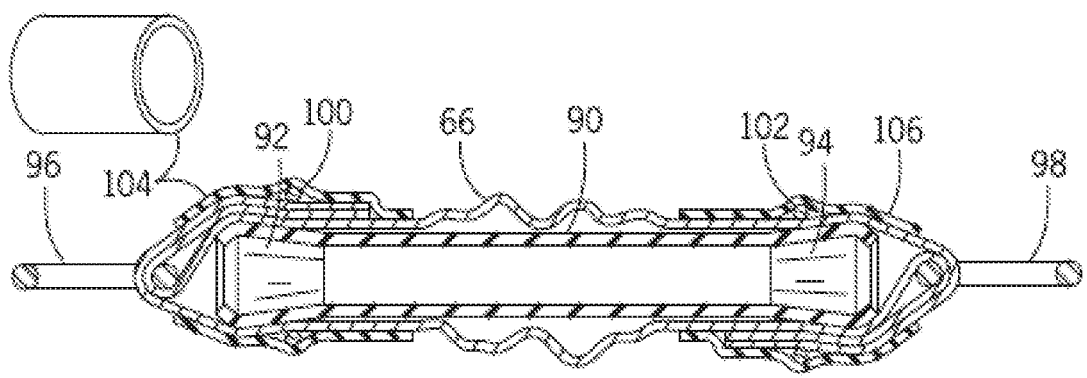
FIG. 14 illustrates another process step in constructing the stretch cord assembly in FIG. 9, according to an embodiment.

FIG. 14 illustrates another process step in constructing the stretch cord assembly 64 in FIG. 9, according to an embodiment. Some of the features in FIG. 14 are the same or similar to some of the features in FIGS. 9-13 as noted by the same reference numbers, unless expressly described otherwise. The process may include covering the first clip 100 with first rubber sleeve 104 and covering the second clip 102 with second rubber sleeve 106.

Figure 15:
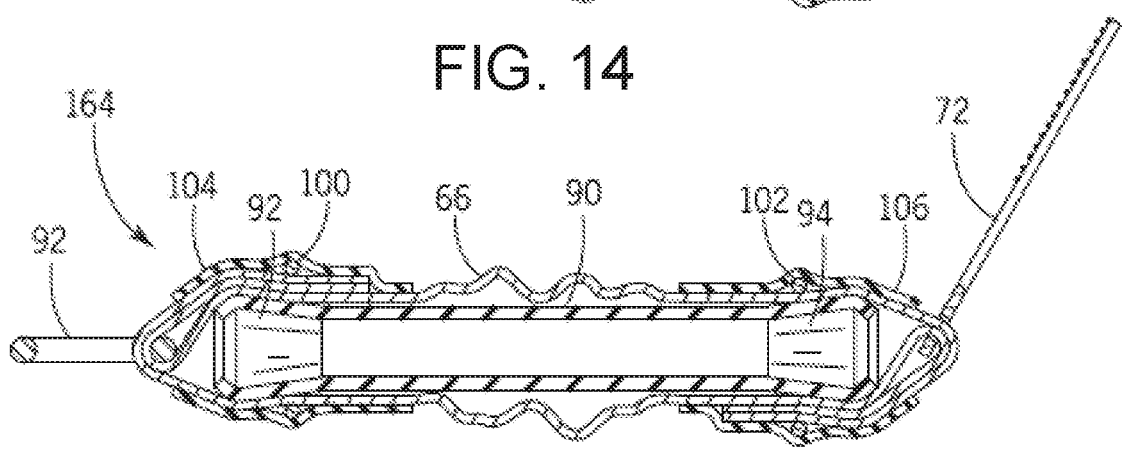
FIG. 15 illustrates a cross-sectional view of a stretch cord assembly, according to an embodiment.

FIG. 15 illustrates a cross-sectional view of a stretch cord assembly 64, according to an embodiment. Some of the features in FIG. 15 are the same or similar to some of the features in FIGS. 9-14 as noted by the same reference numbers, unless expressly described otherwise. In one embodiment, the second ring 98 of the stretch cord assembly 64 may be replaced with first connector 72.

Figure 16:
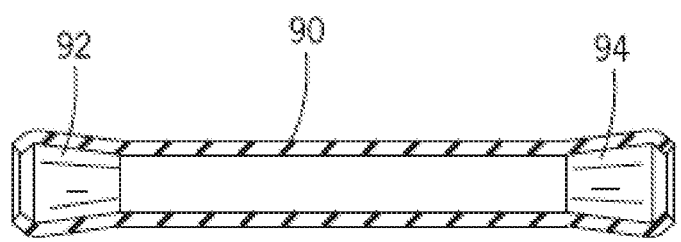
FIG. 16 illustrates a process step in constructing a stretch cord assembly according to an embodiment.

FIG. 16 illustrates a process step in constructing a stretch cord assembly 64 according to an embodiment. Some of the features in FIG. 16 are the same or similar to some of the features in FIGS. 9-15 as noted by the same reference numbers, unless expressly described otherwise. The hollow cord 90 may be wrapped around first retainer end 92 and second retainer end 94.

Figure 17:
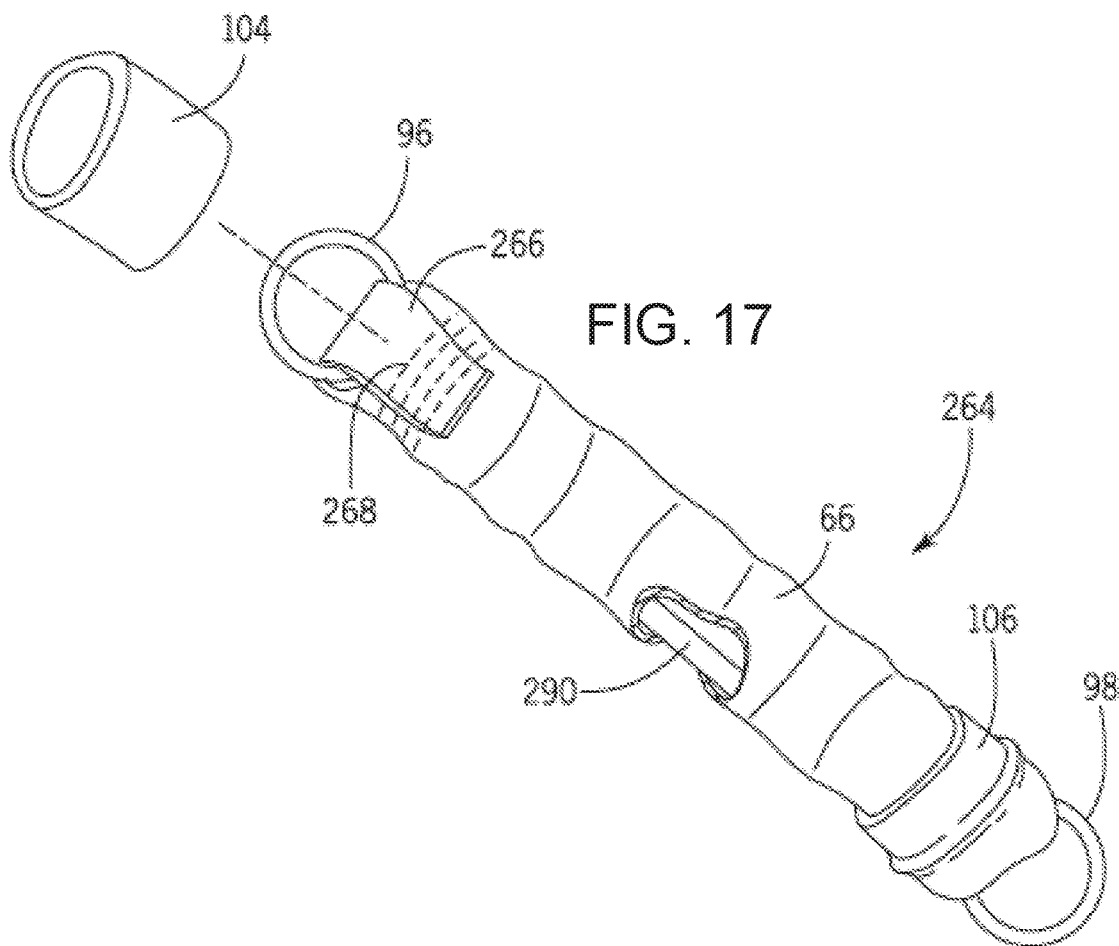
FIG. 17 illustrate a stretch cord assembly that includes an internal cord, according to an embodiment.

FIG. 17 illustrate a stretch cord assembly 264 that includes an internal cord 290, according to an embodiment. Some of the features in FIG. 17 are the same or similar to some of the features in FIGS. 9-16 as noted by the same reference numbers, unless expressly described otherwise. The internal cord 290 may be a shock cord, an elastic cord, a bungee cord, and so forth. In one embodiment, a process of assembling the stretch cord assembly 264 may include sliding the stretch cord sheath 66 over the internal cord 290. The process of assembling the stretch cord assembly 264 may include wrapping the first strap 266 around a first ring 96. The process of assembling the stretch cord assembly 264 may include sewing the first strap 266 to the stretch cord sheath 66 with stitching 268. In another embodiment, the first strap 266 may be a non-stretch fabric that does not deform when under a load. The process of assembling the stretch cord assembly 264 may include wrapping the stretch cord sheath 66 around a second ring 98. In one example, the second clip 102 may be fit over the stretch cord sheath 66. The second clip 102 may provide additional strength and structural integrity to the stretch cord assembly 264. In another embodiment, a first rubber sleeve 104 may cover at least a portion of the first strap 266, such as covering the stitching 268. In another embodiment, the second rubber sleeve 106 may cover at least a portion of the stretch cord sheath 66.

Figure 18:
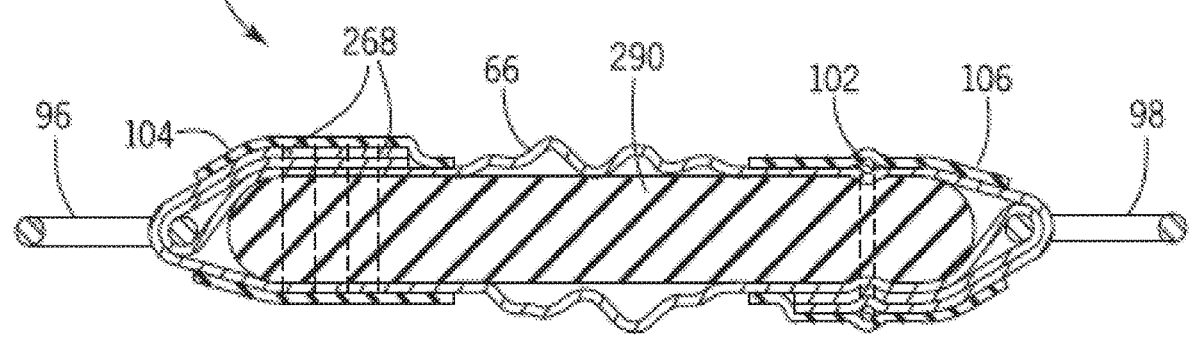
FIG. 18 illustrates a cross-sectional view of the stretch cord assembly in FIG. 17, according to an embodiment.

FIG. 18 illustrates a cross-sectional view of the stretch cord assembly 264 in FIG. 17, according to an embodiment. Some of the features in FIG. 18 are the same or similar to some of the features in FIGS. 9-17 as noted by the same reference numbers, unless expressly described otherwise.

Figure 19A:
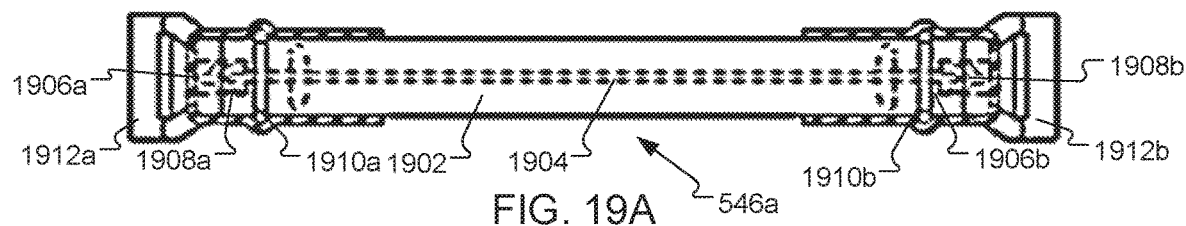
FIG. 19A illustrates stretch cord assembly, according to an embodiment.

FIGS. 19A-E illustrate a variety of stretch cord assemblies 546a-546d to attach to the dynamic cushion heel-ankle-foot orthosis 10 or 200 in FIGS. 1A-ID. FIG. 19A illustrates the stretch cord assembly 546a, according to an embodiment. The stretch cord assembly 546a may include a band 1902, an internal cord 1904, a first buckle end, and a second buckle end. In one embodiment, the stretch cord assembly 546a may include first buckle end with a first internal cord end 1906a, a first pocket 1908a, a first ring 1910a, and a first buckle 1912a. In another embodiment, the stretch cord assembly 546a may include the second buckle end with a second internal cord end 1906b, a second pocket 1908b, a second ring 1910b, and a second buckle 1912b. FIG. 19A illustrates that the first buckle end and the second buckle end may include the same features and may be mirror images of each other.

The band 1902 may be a material with a defined length. In one embodiment, the material of the band 1902 may be leather, plastic, rubber, fabric, and so forth. In another embodiment, the material may be a stretchable material, such as cotton, Spandex®, fleece, Selvedge®, and so forth. When the material of the band 1902 is a stretchable material, the band 1902 may expand to a first length and contract to a second length. In another embodiment, the band 1902 may be a tube, a band, a cord, and so forth. In another embodiment, the band 1902 may be at least partially hollow or include a channel that extends the length of the band 1902.

The band 1902 may also include an internal channel, where the internal cord 1904 may extend from a first end of the band 1902 to a second end of the band 1902. The band 1902 may also include a first pocket 1908a at the first end of the band 1902 and a second pocket 1908b at a second end of the band 1902. The first pocket 1908a may be configured to receive a first end 1906a of the internal cord 1904. In one embodiment, the internal cord 1904 may be made of non-stretchable material and the first pocket 1908a may restrict or limit the length that the internal cord 1904 may extend or contract at the first end of the band 1902. For example, the first end 1906a of the internal cord 1904 may extend to an outer edge of the first pocket 1908a and may contract in length to the inner edge of the first pocket 1908a. The second pocket 1908b may be configured to receive a second end 1906b of the internal cord 1904. The second pocket 1908b may restrict or limit the length that the internal cord 1904 may extend or contract at the second end of the band 1902. For example, the second end 1906b of the internal cord 1904 may extend to an outer edge of the second pocket 1908b and may contract in length to the inner edge of the second pocket 1908b.

The band 1902 with the internal cord 1904 may restrict a length that the stretch cord assembly 546a may extend to. For example, the internal cord 1904 may have a maximum length that the internal cord 1904 may extend to within the first pocket 1908a and the second pocket 1908b. Restricting the length of the stretch cord assembly 546a may restrict an amount the dynamic cushion heel-ankle-foot orthoses as illustrated in FIGS. 1A-1D may rotate or move.

The stretch cord assembly 546a may include the first ring 1910a and the second ring 1910b. In one embodiment, the first ring 1910a may reinforce the first pocket 1908a to keep the first end 1906a of the internal cord 1904 from contracting beyond a first defined point. In another embodiment, the second ring 1910b may reinforce the second pocket 1908b to keep the second end 1906b of the internal cord 1904 from contracting beyond a second defined point.

The stretch cord assembly 546a may include the first buckle 1912a at the first end of the band 1902 and a second buckle 1912b on the second end of the band 1902. The first buckle 1912a and the second buckle 1912b may be used to attach the stretch cord assembly 546a to various buckles, attachments, fasteners, parts, or portions of the dynamic cushion heel-ankle-foot orthoses as illustrated in FIGS. 1A-ID.

Figure 19B:
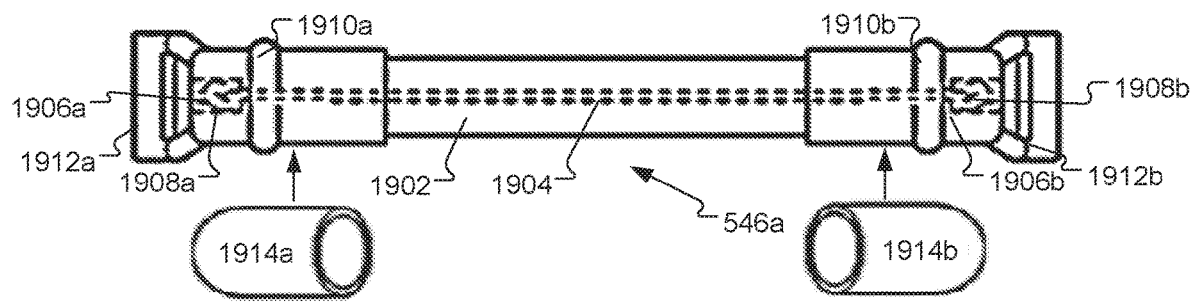
FIG. 19B illustrates the stretch cord assembly with covers, according to an embodiment.

FIG. 19B illustrates the stretch cord assembly 546a with covers 1914a and 1914b, according to an embodiment. Some of the features in FIG. 19B are the same or similar to some of the features in FIG. 19A as noted by the same reference numbers, unless expressly described otherwise. In one embodiment, a first cover 1914a may be attached to the first end of the band 1902 to cover, protect, and/hide the portion of the first end of the band 1902 and the first ring 1910a. In one embodiment, a second cover 1914b may be attached to the second end of the band 1902 to cover, protect, and/hide the portion of the second end of the band 1902 and the second ring 1910b.

Figure 19C:
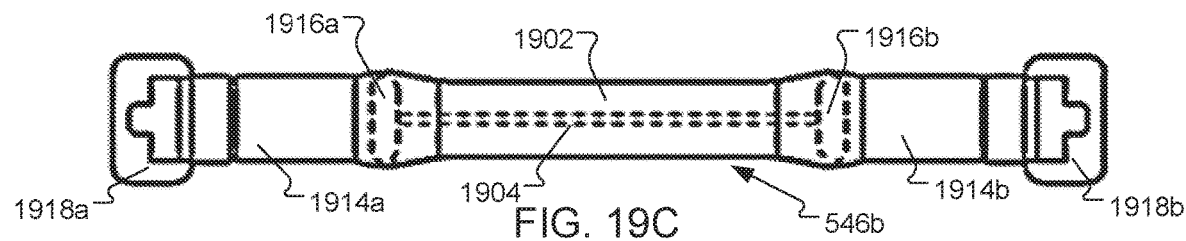
FIG. 19C illustrates the stretch cord assembly with the internal cord with integrated ends, according to an embodiment.

FIG. 19C illustrates the stretch cord assembly 546b with the internal cord 1904 with integrated ends 1916a and 1916b, according to an embodiment. Some of the features in FIG. 19C are the same or similar to some of the features in FIGS. 19A-B as noted by the same reference numbers, unless expressly described otherwise. In one embodiment, the internal cord 1904 may include a first integrated end 1916a that is integrated into a portion of the first end of the band 1902. In another embodiment, the internal cord 1904 may include a second integrated end 1916b that is integrated into a portion of the second end of the band 1902. The first integrated end 1916a and the second integrated end 1916b may be fixed to internal portions of the band 1902 such that the band 1902 may not expand or contract.

In another embodiment, the first buckle 1918a may be attached to the first end of the band 1902 and the second buckle 1918b may be attached to the second end of the band 1902. The first buckle 1918a and the second buckle 1918b may be adjustably attached to various buckles, attachments, fasteners, parts, or portions of the dynamic cushion heel-ankle-foot orthoses as illustrated in FIGS. 1A-ID.

Figure 19D:
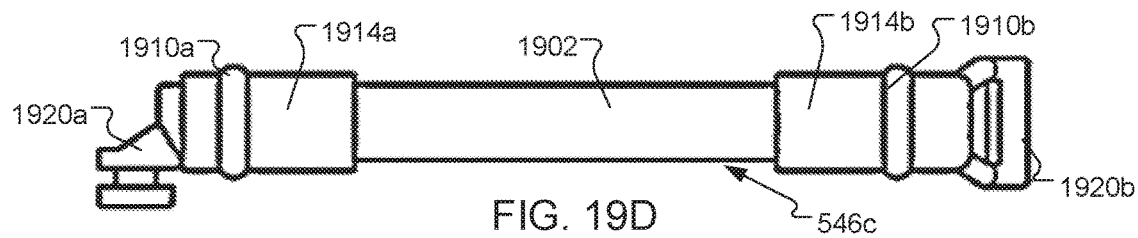
FIG. 19D illustrates the stretch cord assembly a first buckle and a second buckle, according to an embodiment.

FIG. 19D illustrates the stretch cord assembly 546c a first buckle 1920a and a second buckle 1920b, according to an embodiment. Some of the features in FIG. 19D are the same or similar to some of the features in FIGS. 19A-C as noted by the same reference numbers, unless expressly described otherwise. In one embodiment, the stretch cord assembly 546c may not include the internal cord 1904 and the band 1902 may be made of non-stretchable material. The stretch cord assembly 546c may also include a first buckle 1920a that is attached to the first end of the band 1902. For example, the first buckle 1920a may be attached to the first end of the band 1902 by an adhesive, welding, heat, and so forth. The first end of the band 1902 and/or the first buckle 1920a may be covered by the first cover 1914a. In one embodiment, the first cover 1914a may be fastened to the band 1902 by the first ring 1910a.

The stretch cord assembly 546c may also include a second buckle 1920b that is attached to the second end of the band 1902. For example, the second buckle 1920b may be attached to the second end of the band 1902 by an adhesive, welding, heat, and so forth. The second end of the band 1902 and/or the second buckle 1920b may be covered by the second cover 1914b. In one embodiment, the second cover

1914*b* may be fastened to the band 1902 by the second ring 1910*b*. In one embodiment, the first buckle 1920*a* may be the same type of buckle as the second buckle 1920*b*. In another embodiment, the first buckle 1920*a* may be a different type of buckle than the second buckle 1920*b*. The first buckle 1920*a* and/or the second buckle 1920 may be adjustably attached to various buckles, attachments, fasteners, parts, or portions of the dynamic cushion heel-ankle-foot orthoses as illustrated in FIGS. 1A-1D. For example, as discussed below, the first buckle 1920*a* may be inserted into different slots in the leg calf shell 12 to adjust the length of the stretch cord assembly 546*c* and thereby loosen to tighten different portions of the dynamic cushion heel-ankle-foot orthoses as illustrated in FIGS. 1A-1D.

Figure 19E:
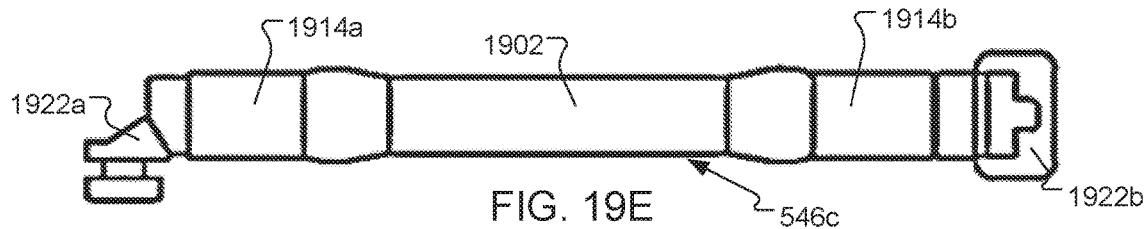
FIG. 19E illustrates the stretch cord assembly a first buckle and a second buckle, according to an embodiment.

FIG. 19E illustrates the stretch cord assembly 546*c*, a first buckle 1922*a*, and a second buckle 1922*b*, according to an embodiment. Some of the features in FIG. 19E are the same or similar to some of the features in FIGS. 19A-D as noted by the same reference numbers, unless expressly described otherwise. In one embodiment, the first buckle 1922*a* and the second buckle 1922*b* may be integrally attached to the band 1902. For example, a band 1902, the first buckle 1922*a*, and the second buckle 1922*b* may be formed out of a single piece of material, such as via molding, casting, or three dimensional (3D) printing. In another embodiment, the first buckle 1922*a* may be attached to the first end of the band 1902 by the first cover 1914*a* and the second buckle 1922*b* may be attached to the second end of the band 1902 by the second cover 1914*b*.

FIG. 20A-D illustrate a process for making a stretch cord assembly 564*a*. The process for making the stretch cord assembly 564*a* may include the following steps. The order of the steps is not intended to be limiting and may vary. A similar process may be used for making the stretch cord assembly 564*b* in FIG. 19C and/stretch cord assembly 564*c* in FIGS. 19D-E.

Figure 20A:
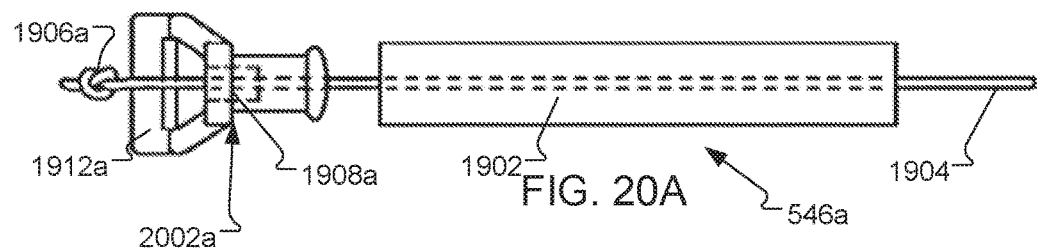
FIG. 20A illustrates a process step of assembling a portion of the stretch cord assembly, according to an embodiment.

FIG. 20A illustrates a process step of assembling a portion of the stretch cord assembly 564*a*, according to an embodiment. Some of the features in FIG. 20A are the same or similar to some of the features in FIG. 19A-B as noted by the same reference numbers, unless expressly described otherwise. The stretch cord assembly 564*a* may include the first buckle 1912*a*, the internal cord 1905, and a first retainer end 2002*a*. The first retainer end 2002*a* may include a portion of the band 1902 with the first pocket 1908*a*. The internal cord 1904 may be inserted through the first pocket 1908*a*, the portion of the band 1902 of the first retainer end 2002*a*, and the remaining portion of the band 1902. The first buckle 1912*a* may also be attached to the portion of the band 1902 of the first retainer end 2002*a*.

Figure 20B:
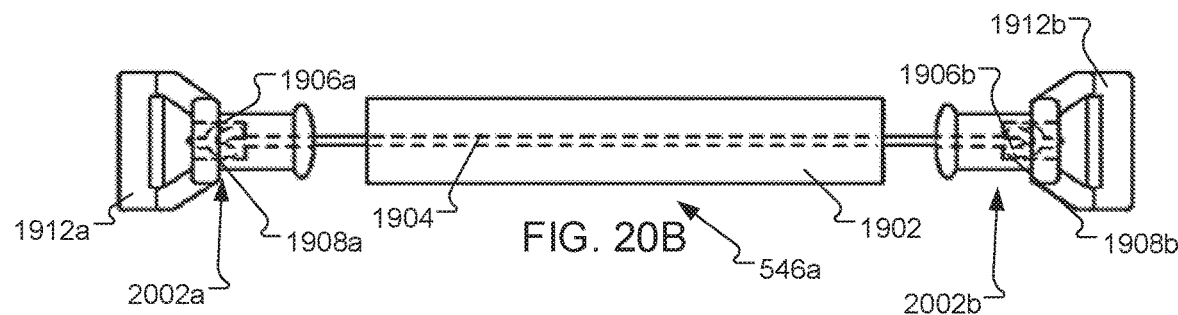
FIG. 20B illustrates another process step of assembling a portion of the stretch cord assembly, according to an embodiment.

FIG. 20B illustrates another process step of assembling a portion of the stretch cord assembly 564*a*, according to an embodiment. Some of the features in FIG. 20B are the same or similar to some of the features in FIGS. 19A-B and 20A as noted by the same reference numbers, unless expressly described otherwise. As discussed above, the stretch cord assembly 564*a* may include the first buckle 1912*a*, the internal cord 1904, and a first retainer end 2002*a*. The stretch cord assembly 564*a* may also include the second buckle 1912*b* and a second retainer end 2002*b*. The second retainer end 2002*b* may include a second portion of the band 1902 with the second pocket 1908*b*. The internal cord 1904 may be inserted into the second portion of the band 1902 of the second retainer end 2002*b* toward the second pocket 1908*b*. The second buckle 1912*b* may also be attached to the second portion of the band 1902 of the second retainer end 2002*b*.

Figure 20C:
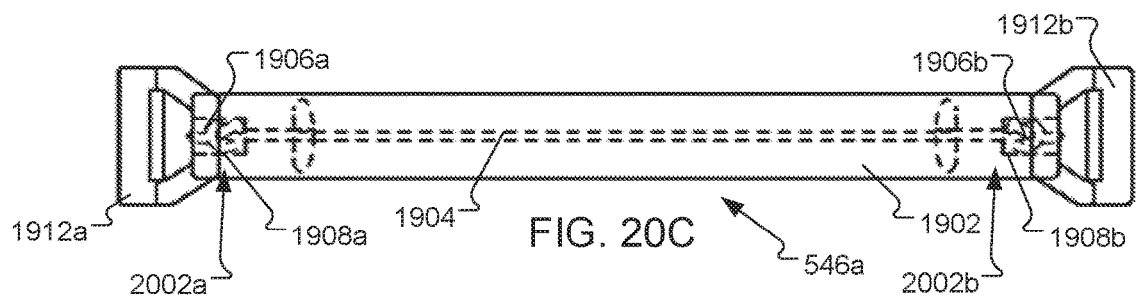
FIG. 20C illustrates another process step of assembling a portion of the stretch cord assembly, according to an embodiment.

FIG. 20C illustrates another process step of assembling a portion of the stretch cord assembly 564*a*, according to an embodiment. Some of the features in FIG. 20C are the same or similar to some of the features in FIG. 19A-20B as noted by the same reference numbers, unless expressly described otherwise. When the internal cord 1904 is attached to the first retainer end 2002*a* and the second retainer end 2002*b*, the internal cord 1904 may contract to pull the first buckle 1912*a* to a first end of the band 1902 and the second buckle 1912*b* to a second end of the band 1902.

Figure 20D:
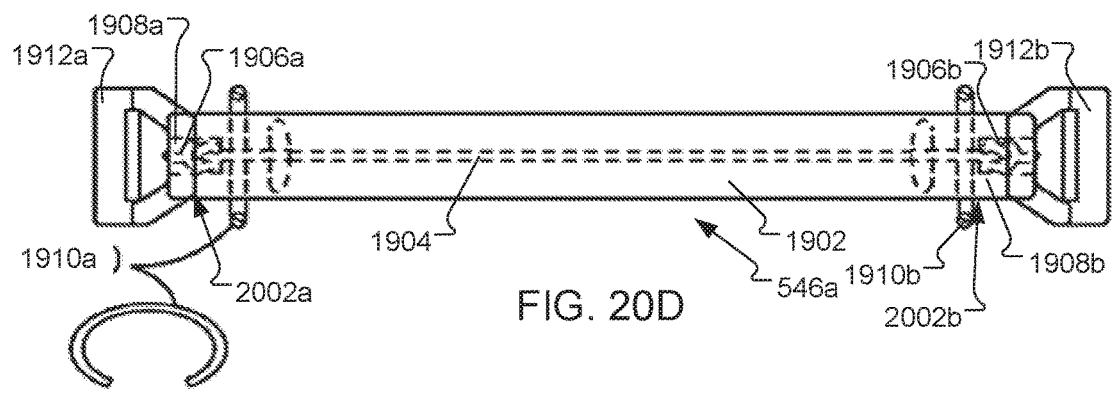
FIG. 20D illustrates another process step of assembling a portion of the stretch cord assembly, according to an embodiment.

FIG. 20D illustrates another process step of assembling a portion of the stretch cord assembly 564*a*, according to an embodiment. Some of the features in FIG. 20D are the same or similar to some of the features in FIG. 19A-20C as noted by the same reference numbers, unless expressly described otherwise. When the internal cord 1904 has contracted it pulls the first buckle 1912*a* to a first end of the band 1902 and the second buckle 1912*b* to a second end of the band 1902. The first ring 1910*a* may be attached approximate to the first end of the band 1902 and the second ring 1910*b* may be attached approximate to the second end of the band 1902 to keep the second retainer end 2002*b* in place so that the stretch cord assembly 564*a* extends and contracts within a defined length range.

Figure 21A:
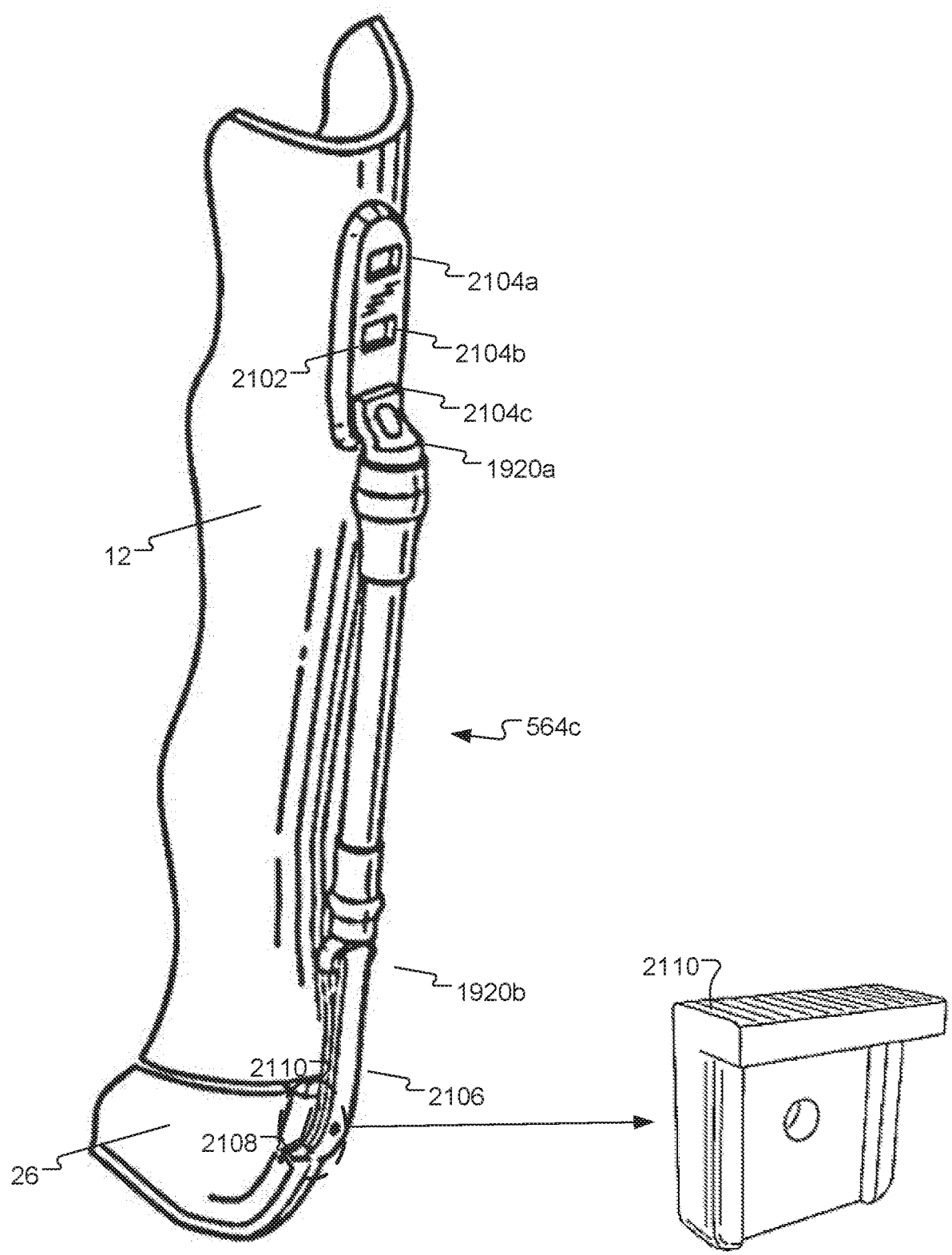
FIG. 21A illustrates a back portion of the leg calf shell and a heel portion of the boot shell connected together by the stretch cord assembly, according to an embodiment.

FIG. 21A illustrates a back portion of the leg calf shell 12 and a heel portion of the boot shell 26 connected together by the stretch cord assembly 564*c*, according to an embodiment. Some of the features in FIG. 21A are the same or similar to some of the features in FIGS. 1A-D and 19A-19E as noted by the same reference numbers, unless expressly described otherwise. As discussed above, the stretch cord assembly 564*c* may connect the back portion of the leg calf shell 12 and the heel portion of the boot shell 26. In one embodiment, the back portion of the leg calf shell 12 may include a buckle attachment 2102 with one or more slots to receive the first buckle 1920*a*. In one example, the buckle attachment 2102 may include a first slot 2104*a*, a second slot 2104*b*, and a third slot 2104*c*. The first buckle 1920*a* may include a block end that may be configured to be inserted into one of the slots 2104*a-c*. In one example, the block end of the first buckle 1920*a* may be inserted into the first slot 2104*a* and remain attached to the buckle attachment 2102 via a friction fit. In another example, the block end of the first buckle 1920*a* may be rotated to a first orientation to be inserted into the first slot 2104*a* and then rotated to a second orientation to lock the block end in place so that it is fastened to the buckle attachment 2102.

The heel portion of the boot shell 26 may include a strap 2106 connected to the heel portion by a fastener 2108. The strap 2106 may be attached to the second buckle 1920*b* of the stretch cord assembly 564*c*. In one embodiment, the strap 2106 may be fixedly fastened to the second buckle 1920*b* such that the strap 2106 may not be removed from the second buckle 1920*b*. The strap 2106 may then be fastened to the fastener 2108 by a friction fit, a rivet, a screw, epoxy, an adhesive, a clamp, or another type of fastener. In another embodiment, the strap 2106 may be fixedly fastened to the fastener 2108 such that the strap 2106 may not be removed from the fastener 2108. The strap 2106 may then be fastened to the second buckle 1920*b* by a friction fit, a rivet, a screw, epoxy, an adhesive, a clamp, or another type of fastener. In another embodiment, a first end of the strap 2106 may be fastened to the fastener 2108 and a second end of the strap may be inserted through an opening of the second buckle 1920*b* and then also fastened to the fastener 2108. In another embodiment, the fastener 2108 may include a portion 2110 that may extend from the fastener 2108 to fit between the heel portion of the boot shell 26 and the back portion of the leg calf shell 12 to separate the heel portion of the boot shell 26 from the back portion of the leg calf shell 12.

Figure 21B:
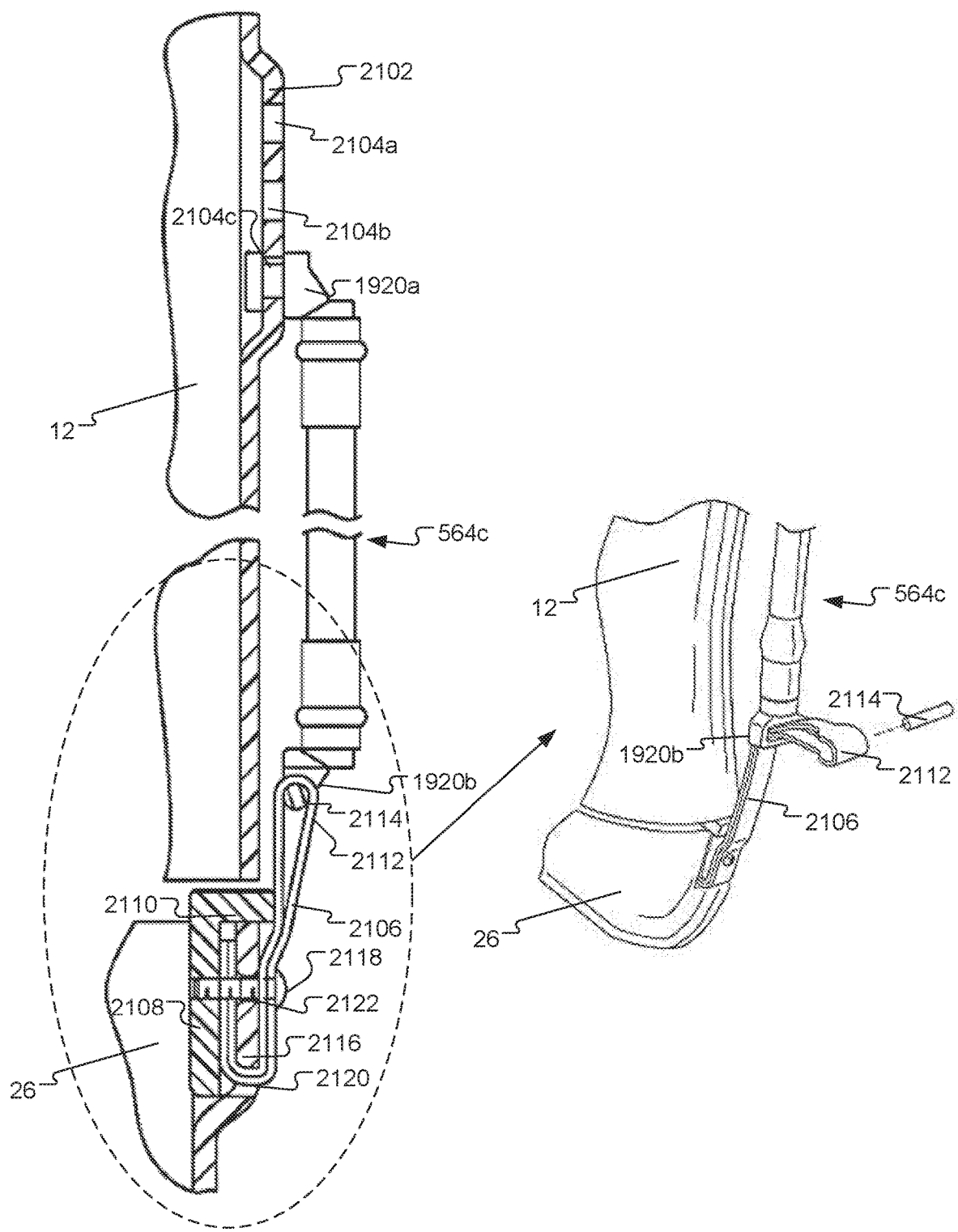
FIG. 21B illustrates an exposed view of the back portion of the leg calf shell and a heel portion of the boot shell connected together by the stretch cord assembly, according to an embodiment.

FIG. 21B illustrates an exposed view of the back portion of the leg calf shell 12 and a heel portion of the boot shell 26 connected together by the stretch cord assembly 564c, according to an embodiment. Some of the features in FIG. 21B are the same or similar to some of the features in FIGS. 1A-D, 19A-19E, and 21A as noted by the same reference numbers, unless expressly described otherwise.

As discussed above, the stretch cord assembly 564c may be connected to the strap 2106 in order to connect the back portion of the leg calf shell 12 to the heel portion of the boot shell 26. In one embodiment, a first end of the strap 2106 and a second end of the strap 2106 may be fastened to the fasteners 2108 to form a loop end 2112. The loop end 2112 of the strap 2106 may be inserted into an opening of the second buckle 1920b. To secure the strap 2106 to the second buckle 1920b, a peg 2114 may be inserted into the loop end 2112 of the strap 2106 so that a diameter of the loop end 2112 is greater in size than the opening of the second buckle 1920b such that the loop end 2112 may not go back through the opening of the second buckle 1920b. The configuration of the loop end 2112 with the peg 2114 may allow the stretch cord assembly 564c to be removably attached to the heel portion of the boot shell 26. For example, when the portion 2110 is removed from the loop end 2112, the loop end 2112 may be disconnected from the second buckle and the first buckle 1920a may be removed from the first slot 2104a to allow the stretch cord assembly 564c to be removed and/or replaced.

In one embodiment, to connect the strap 2106 to the heel portion of the boot shell 26, the fastener 2108 may include a locking portion 2116 that may be attached to the fastener 2108. The locking portion 2116 may include a slot 2120 to receive an end of the strap 2106 that connects to the heel portion of the boot shell 26 and an opening 2122 to receive a holder 2118. The holder 2118 may be a rivet, a bolt, a screw, a clasp, a snap, and so forth. In one embodiment, once the end of the strap 2106 that connects to the heel portion of the boot shell 26 is inserted into the slot 2120, the holder 2118 may be inserted into the opening 2122 to secure the strap 2106 to the heel portion of the boot shell 26. The thick of the portion 2110 may vary to increase or decrease an amount of separation between the bottom of the leg calf shell 12 and the top of the boot shell 26. For example, as the thickness of the portion 2110 increase, the separation between the bottom of the leg calf shell 12 and the top of the boot shell 26 may increase. In another embodiment, the holder 2118 may connect directly to the back of the boot shell 26 instead of connecting to the fastener 2108.

The term "a" or "an" means "at least one" or "one or more." The term "about" or "approximately" refers to a range of values within plus or minus 10% of the specified number. The term "substantially" means that the actual value is within about 10% of the actual desired value, particularly within about 5% of the actual desired value and especially within about 1% of the actual desired value of any variable, element or limit set forth herein.

The disclosure above encompasses multiple distinct embodiments with independent utility. While these embodiments have been disclosed in a particular form, the specific embodiments disclosed and illustrated above are not to be considered in a limiting sense as numerous variations are possible. The subject matter of the embodiments includes the novel and non-obvious combinations and sub-combinations of the various elements, features, functions and/or properties disclosed above and inherent to those skilled in the art pertaining to such embodiments. Where the disclosure or subsequently filed claims recite "a" element, "a first" element, or any such equivalent term, the disclosure or claims is to be understood to incorporate one or more such elements, neither requiring nor excluding two or more such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower or equal in scope to the original claims, are to be considered within the subject matter of the embodiments described herein.

The invention claimed is:

1. An apparatus, comprising a stretch cord assembly, wherein the stretch cord assembly comprises:
    a sheath;
    a stretch cord extending along an interior of the sheath from a first end of the sheath to a second end of the sheath, wherein the sheath covers at least a middle portion of the stretch cord;
    a first pocket configured to receive a first end of the stretch cord;
    a first buckle attached to the first pocket;
    a first sleeve configured to cover at least a portion of the first end of the stretch cord;
    a first clip configured to fasten the first sleeve around the first end of the sheath;
    a second pocket configured to receive a second end of the stretch cord;
    a second buckle attached to the second pocket;
    a second sleeve configured to cover at least a portion of the second end of stretch cord; and
    a second clip configured to fasten the second sleeve around the first end of the sheath.

2. The apparatus of claim 1, wherein:
    the first end of the stretch cord includes a first knot held within a cavity of the first pocket; and
    the second end of the stretch cord includes a second knot held within a cavity of the second pocket.

3. The apparatus of claim I, wherein:
    the first buckle is configured to connect to a first strap; and
    the second end of the stretch cord assembly is configured to connected to a second strap.

4. The apparatus of claim 3, wherein:
    the first strap is attached to a top portion of a boot; and
    the second strap is attached to a bottom portion of the boot.

5. The apparatus of claim 4, wherein:
    the top portion of the boot comprises a leg calf shell; and
    the bottom portion of the boot comprises a boot shell.

6. The apparatus of claim 4, wherein:
    the first strap includes a first fastener to connect the first strap to the first buckle; and
    the second strap includes a second fastener to connect the second strap to the second buckle.

7. The apparatus of claim 1, wherein:
    the first buckle is at least one of a first loop, a first ring, a first clasp, or a third clip; and the second buckle is at least one of a second loop, a second ring, a second clasp, or a fourth clip.

8. The apparatus of claim 1, wherein:
the first clip is adapted to provide additional strength and structural integrity to the stretch cord assembly; and
the second clip is adapted to provide additional strength and structural integrity to the stretch cord assembly.

9. The apparatus of claim 1, wherein:
the first sleeve is configured to cover stitching between the first buckle and the first pocket; and
the second sleeve is configured to cover stitching between the second buckle and the second pocket.

10. The apparatus of claim 1, wherein the stretch cord is a shock cord, an elastic cord, or a bungee cord.

11. The apparatus of claim 1, wherein a material of the sheath is a stretchable material such that the sheath may expand to a first length and contract to a second length.

12. The apparatus of claim 1, wherein the sheath is a tube, a band, or a cord.

13. The apparatus of claim 1, wherein the sheath is least partially hollow to provide a channel that extends a length of the sheath.

14. The apparatus of claim 1, wherein the stretch cord is configured to:
extend to an outer edge of the first pocket and contract in length to an inner edge of the first pocket; and
extend to an outer edge of the second pocket and contract in length to an inner edge of the second pocket.

15. The apparatus of claim 1, wherein:
the first ring is configured to reinforce the first pocket to keep the first end of the stretch cord from contracting beyond a first defined point; and
the second ring is configured to reinforce the second pocket to keep the second end of the stretch cord from contracting beyond a second defined point.

16. A device, comprises:
a sheath;
a stretch cord extending along an interior of the sheath from a first end of the sheath to a second end of the sheath;
a first buckle attached to a first end of the stretch cord;
a first sleeve configured to cover at least a portion of the first end of stretch cord;
a first clip configured to fasten the first sleeve around the first end of the sheath;
a second buckle attached to a second end of the stretch cord;
a second sleeve configured to cover at least a portion of the second end of the stretch cord; and
a first integrated end fixed internally within a first end of the sheath and a second integrated fixed internally within a second end of the sheath end fixed internal such that the stretch cord does not expand or contract.

17. The device of claim 16, wherein a material of the stretch cord is a stretchable material to allow the sheath to expand to a first length and contract to a second length.

* * * * *